United States Patent [19]

Jenden et al.

[11] Patent Number: 4,468,742
[45] Date of Patent: Aug. 28, 1984

[54] MICROPROCESSOR SYSTEM FOR QUANTITATIVE CHROMATOGRAPHIC DATA ANALYSIS

[75] Inventors: Donald J. Jenden, Malibu; Robert W. Silverman, Los Angeles; Frederick C. Lee, South Pasadena, all of Calif.

[73] Assignee: The Regents of University of California, Berkeley, Calif.

[21] Appl. No.: 244,761

[22] Filed: Mar. 17, 1981

[51] Int. Cl.³ .......................................... G06F 15/20
[52] U.S. Cl. ................................. 364/497; 364/571
[58] Field of Search ............... 364/497, 498, 200, 900, 364/571; 73/23.1

[56] References Cited

U.S. PATENT DOCUMENTS

| | | | |
|---|---|---|---|
| 3,562,501 | 2/1971 | Mears | 364/497 |
| 3,614,409 | 10/1971 | Watkin | 364/487 |
| 3,986,011 | 10/1976 | Poole et al. | 364/200 X |
| 4,180,857 | 12/1979 | Yoshihara et al. | 364/497 |
| 4,229,968 | 10/1980 | Muldoon | 364/497 X |
| 4,338,811 | 7/1982 | Miyagi et al. | 364/498 X |
| 4,357,668 | 11/1982 | Schwartz et al. | 364/497 |

*Primary Examiner*—Edward J. Wise
*Attorney, Agent, or Firm*—Poms, Smith, Lande & Rose

[57] ABSTRACT

Quantitative chromatography is widely used in many fields to measure the amount of a compound present in a mixture. A series of Gaussian-like peaks are generated as output, and the size is conventionally measured by peak area or peak height determinations. The microprocessor-based analysis system of the present invention is designed to "learn" the characteristics of a set of chromatographic peaks. Retention time and peak width parameters are used to detect and measure selected peaks by a convolution procedure based on a matched filter. The filter is applied to peaks in the neighborhood of selecting peak times which have a shape closely resembling that of a control sample. The system is built around a microprocessor with a wide dynamic range analog-to-digital conversion input stage. Operator interaction with the programs and the printing of output results is facilitated.

23 Claims, 29 Drawing Figures

MICROPROCESSOR SYSTEM FOR QUANTITATIVE CHROMATOGRAPHIC DATA ANALYSIS

The invention described herein was made in the course of, or under, a grant from the United States Public Health Service.

BACKGROUND OF THE INVENTION

The present invention relates to methods and apparatus for performing quantitative analysis and, more particularly, to chromatography and the like.

Chromatographic instrumentation is extensively used for qualitative chemical analysis in the fields of medicine, pharmacology, toxicology, environmental monitoring, the petrochemical industry, and good production and quality control. The two types of instruments most widely used to perform these analyses are chromatographs and liquid chromatographs. Both utilize a specially prepared column to perform a physical separation of two or more compounds based upon their differential distribution between two phases; of which one is stationary and the other fluid. In addition to the column, a means must be provided to deposit the sample mixture on the column and to detect each component as it sequentially elutes from the column. The detector ideally provides an electrical output signal which is proportional to the quantity per unit time of the eluting sample components. The output signal over the period of the sample analysis is a series of peaks which are approximately Gaussian in shape, displayed on a potentiometric recorder or plotted from reconstructed digitized data. To relieve the investigator from the tedious and time consuming task of measuring the size of these peaks, many automatic measuring devices have been developed over the last 15 years. The first devices available were most commonly voltage-to-frequency converters coupled to counters with appropriate start/stop gating. As low cost microprocessors became available, these devices evolved into sophisticated digital signal processors.

The chromatographic data analysis systems that are presently on the market perform either or both a peak height or peak area measurement. These approaches are essentially automated versions of the traditional manually performed graphical methods. Consequently, these techniques can be generally applied to process any chromatographic peak, providing the signal-to-noise ratio is good. This requirement is necessary because peak height and area measurements are dependent on accurately defining the baseline upon which the peak is measured. Difficulty arises when the peak is small or asymetric or when the baseline is sloping or especially curved. Each of these problems must be individually handled by the data processor. Commercially available chromatographic analysis systems make extensive use of sometimes elaborate logic to extract meaningful data from what may be a poor quality chromatographic run. Equally important is the need to recognize the correct time within the sample run to apply the appropriate algorithm. The advent of microprocessor technology has considerably increased the performance-to-cost ratio for these more sophisticated versions. However, given the computation capability now available in relatively low cost microprocessor systems, a totally different approach becomes feasible for the measurement of chromatographic peaks.

A large number of applications involving the use of chromatographic instrumentation and the like require quantitative analysis on repetitive samples. Examples for the use of such analysis would be assays of a drug or drug metabolite in blood or urine, hospital clinical laboratory screening procedures, industrial process control and quality control, environmental pollution studies, and forensic applications. Each component can be recognized by its retention time. Quantitation can be based on the relative size of each peak to that of an internal standard, a related compound which is added to the sample initially in a precisely known amount. Data reduction can be optimized by estimation with maximum precision of the sizes of peaks appearing at pre-established times.

Wherefore, it is the object of the present invention to provide an improved method and apparatus for analysis by chromatography, or the like, which provides a best estimate of sample analysis by learning sample characteristics and applying them to later analysis.

SUMMARY

The foregoing objectives have been attained in the quantitative analysis of a series of samples as to the contents thereof in apparatus producing an output signal reflecting the quantity of a component as a peak of substantially Gaussian shape at a fixed time associated with the component by the improved method comprising the steps of injecting into the apparatus a standard sample containing a known amount of the compound to be analyzed, measuring the time to the output of a signal peak associated with the compound to be analyzed to establish the retention time of the apparatus associated therewith, saving the established retention time, establishing a data filter by scaling a Gaussian based curve to the curve of the signal peak, injecting into the apparatus a series of samples containing unknown amounts of the compound to be analyzed, for each sample of the series, sequentially convolving the data filter to the output signal for a sequence of time divisions on either side of and in close proximity to the saved retention time following the injection of the sample to establish a figure of merit reflecting the relationship of the size of the output signal waveform to the data filter curve, and, establishing the quantity of component for each of the samples of the series as a function of the figure of merit relative to the known quantity in the standard sample.

In the preferred embodiment, the method further includes establishing a correlation coefficient reflecting the accuracy of the best fit curve from the data filter used to establish the figure of merit whereby the probability of the figure of merit being an accurate reflection of the quantity of the component in the sample can be determined.

In the preferred embodiment, the data filter is a finite impulse response filter and has the shape of a second differential Gaussian. Further, the data filter has a length of $12\sigma$ and is expressed as $$f(x) = \left(\frac{2}{\sigma}\right)^{3/2} \left(1 - \frac{x^2}{\sigma^2}\right) e^{-\frac{x^2}{2\sigma^2}}$$

For preferred results, the data is convolved for a window about the retention time derived to give $19\sigma$ around the retention time.

The correlation coefficient r is employed with the variance ratio F which is expressed as $$F_{n-2,1} = \frac{(n-2)r^2}{1-r^2}$$

The method of the present invention is incorporated in apparatus for the quantitative analysis of samples as to the contents thereof wherein the apparatus has an input for the injection of a sample and an output producing a signal reflecting the quantity of a component as a peak of substantially Gaussian shape at a fixed time associated with the component following injection, by the improvement thereto for allowing rapid and accurate analysis of series of samples for the same component comprising means operatively connected to the apparatus for an operator to designate whether a sample being analyzed is a standard sample or an unknown sample, means operatively connected to the designation means and the output for storing characteristic data about a sample when an operator designates the sample as a standard sample, and, means operatively connected to the designation means, the storing means and the output for calculating a figure of merit related to the quantity of unknown component in a sample as a function of the relationship of the stored standard sample characteristics to the characteristics of the sample's output signal characteristics when an operator designates the sample as an unknown sample whereby the derived value of the unknown component is a function of learned characteristics about such components.

In the preferred embodiment, the characteristic data storage means stores the retention time between injection of the sample and the peak in the output signal associated with the component of interest. Means are also operably connected to the characteritic data storage means for an operator to designate a time window only during which a peak is searched for. The characteristic data storage means stores data associated with the shape of the curve of the peak for the component of interest. In particular, the characteristic data storage means stores parameters defining a Gaussian based curve which is a second differential Gaussian. The calculating means employs a finite impulse response data filter defined by the stored parameters and convolves the filter against unknown sample data to get a best fit to the shape of the peak of the signal for the unknown sample. It is further preferred that the data filter have a length of $12\sigma$ and that the filter function be expressed as $$f(x) = \left(\frac{2}{\sigma}\right)^{3/2} \left(1 - \frac{x^2}{\sigma^2}\right) e^{-\frac{x^2}{2\sigma^2}}$$

The preferred apparatus convolves the data for a window about the retention time derived to give $19\sigma$ around the retention time.

The preferred apparatus also includes means operatively connected to the calculating means for establishing a correlation coefficient reflecting the accuracy of the best fit curve from the data filter used to establish the figure of merit whereby the probability of the figure of merit being an accurate reflection of the quantity of the component in the sample can be determined.

The preferred use of the correlation coefficient r is in the variance ratio F expressed as $$F_{n-2,1} = \frac{(n-2)r^2}{1-r^2}$$

DESCRIPTION OF THE PREFERRED EMBODIMENT

The microprocessor based analysis system of the present invention as described hereinafter is an operational system and is designed to perform quantitative analysis on repetitive samples for the same compounds. All communication with the programs is carried out through a hard copy computer terminal. Dialog with the operator is in English and designed to be easily understood by people untrained in computer use. The hardware is automatically checked and calibrated before starting an analytical run and a dialog with the operator establishes the characteristics of the problem. A standard sample containing a known amount of the compounds to be analyzed is then injected into the chromatographic column. Using a routine called "PFIND", the time is measured between the injection and elution of the components of interest (retention time). Using a second injection of the standard sample, the peak widths at the retention time are measured and retained. In all subsequent samples to be analyzed the information that was "learned" from the standard sample is used to find and measure the chromatographic peak size by convolving the sample data with a filter derived from the standard sample. A correlation coefficient is also computed to provide an indication to the investigator of the reliability of the measurement.

The descriptions which follow hereinafter are of a system according to the present invention as built and tested by the applicants herein. It should be remembered that while the described system was used in conjunction with a chromatograph, it will work with any analysis apparatus producing data in the form of substantially Gaussian peaks.

HARDWARE DESCRIPTION

Figure 1:
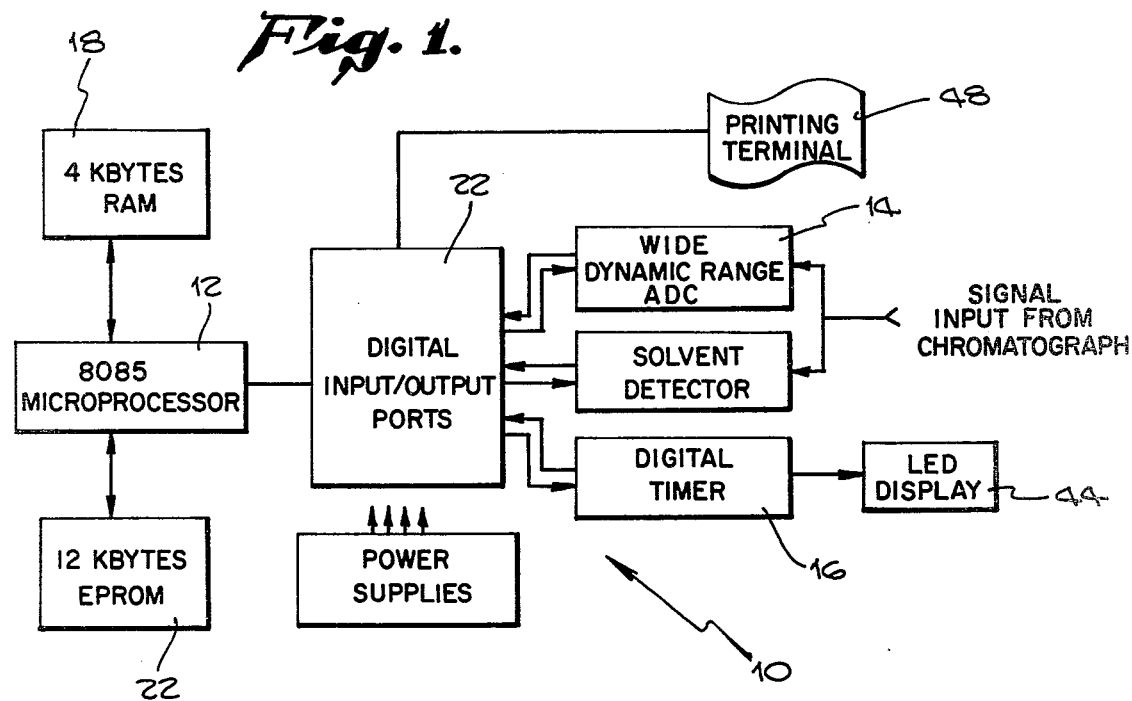
FIG. 1 is a block diagram of the improved data calculating system of the present invention as employed in conjunction with quantitative testing apparatus.

Referring first to FIG. 1, the chromatographic analysis system, generally indicated as 10, utilizes an Intel model 8085 microprocessor 12 with a wide dynamic range analog input stage 14 and peripheral digital seconds timer 16. The microprocessor 12 has access to 4-kbytes of static random access memory (RAM) 18 and 12-kbytes of erasable programmable read only memory (EPROM) 20 for program storage. To accommodate a wide dynamic range signal which can be generated by gas chromatograph detectors ($>10^5$), a novel analog-to-digital conversion technique was implemented which will be described shortly. The microprocessor 12 is provided with 13 digital input/output (I/O) lines and a serial I/O port using a universal asynchronous receiver transmitter, all generally indicated as 22. Four levels of interrupts are provided in the 8085, of which three are used for indicating "data ready", "terminal keyboard receive ready", and "terminal printer ready" in order of descending priority.

Figure 2:
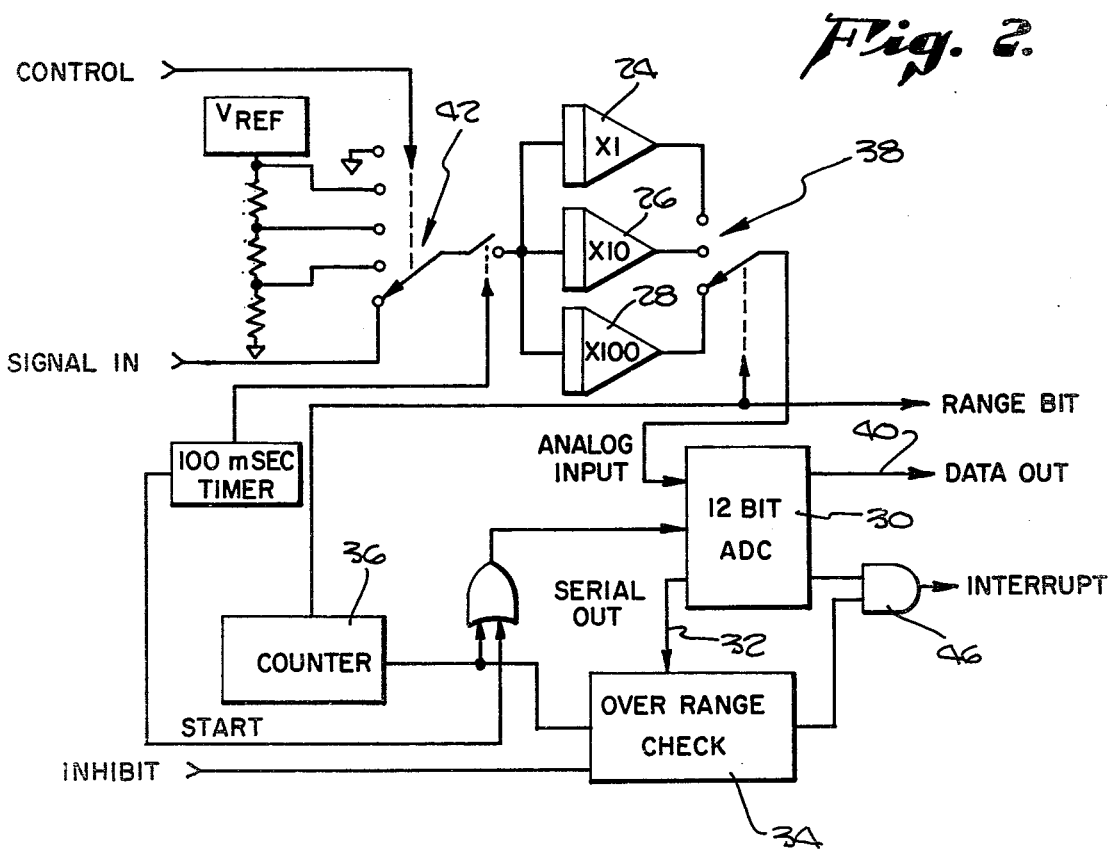
FIG. 2 is a block diagram of the data gathering portion of the system of the present invention.

The analog input stage 14 is schematically illustrated in FIG. 2. Three integrators 24, 26, 28 of sensitivities X1, X10, and X100, respectively, are utilized to integrate the anlog signal simultaneously. After the integration period of nominally 100 ms, the output of the most sensitive integrator 28 is converted by a 12-bit successive approximation analog-to-digital converter (ADC) 30. The serial output 32 of the converter 30 is checked at block 34 for any logic transitions (0 to 1 or 1 to 0). If none occur, an over-range condition exists, the counter 36 is incremented connecting the next lower sensitivity integrator (24 or 26) to the ADC 30 (via switch 38), and another conversion is performed. The process is repeated until a nonsaturated integration is reached. When this happens, a fourteen bit digital word comprising twelve bits of mantissa and two range bits is output at 40 to the digital port 22 on the 8085 data bus. This scheme has the advantage of providing a dynamic range of $>10^5$ with only a single microprocessor data input operation. All analog hardware is checked and calibrated automatically under microprocessor control using the control and inhibit lines. Switch 42 is used to select the appropriate reference voltage or ground as signal inputs allowing the actual sensitivities and offsets of each integrator 24, 26, 28 to be measured. Each digitized analog data point is subsequently corrected before being stored. The overall linearity of the wide dynamic range input stage is within one least significant bit.

Data points are collected at fixed intervals of 100 ms times synchronously to 60 Hz mains. Data collection can be initiated in one of two ways. In a gas chromatographic run, a distinct solvent peak is usually present shortly after the sample is injected and provides the preferred method of time measurement initiation. This rapidly increasing, high amplitude signal is detected by a differentiator and comparator and used to signal the microprocessor 12 via a digital input line that data collection should begin. A contact closure provides an alternative means of signaling when a run begins, and can be provided for situations in which an easily recognizable solvent peak is not present. This is usually the case in a liquid chromatographic analysis. A microswitch mounted on the injector valve can generate the start signal. After the microprocessor 12 receives the "start" command, the digital seconds timer 16 with an LED readout 44 indicates the run time and data collection is started. After each point is digitized, an interrupt is signaled by gate 46 to the microprocessor 12 and the data are stored in RAM 18.

The detailed circuit diagrams of the tested embodiment are included herewith as FIGS. 7 through 18. The interrelationships of these circuits and their operation should be apparent to anyone skilled in the art from a review thereof and, accordingly, no attempt is made herein to explain them in detail.

PROGRAM DESCRIPTION

The software of the tested embodiment of the chromatographic analysis system 10 as hereinbefore described is written in a combination of PL/M and assembly language and designed as a dedicated system. As with the hardware, detailed flowcharts are provided herewith as FIGS. 19 through 31, from which anyone skilled in the programming art would be able to code the software applicable to any particular system actually being constructed. Thus, no attempt to describe the flowcharts in detail is undertaken herein. The flowcharts merely accomplish the functions of the method described in general terms hereinafter.

Figure 3:
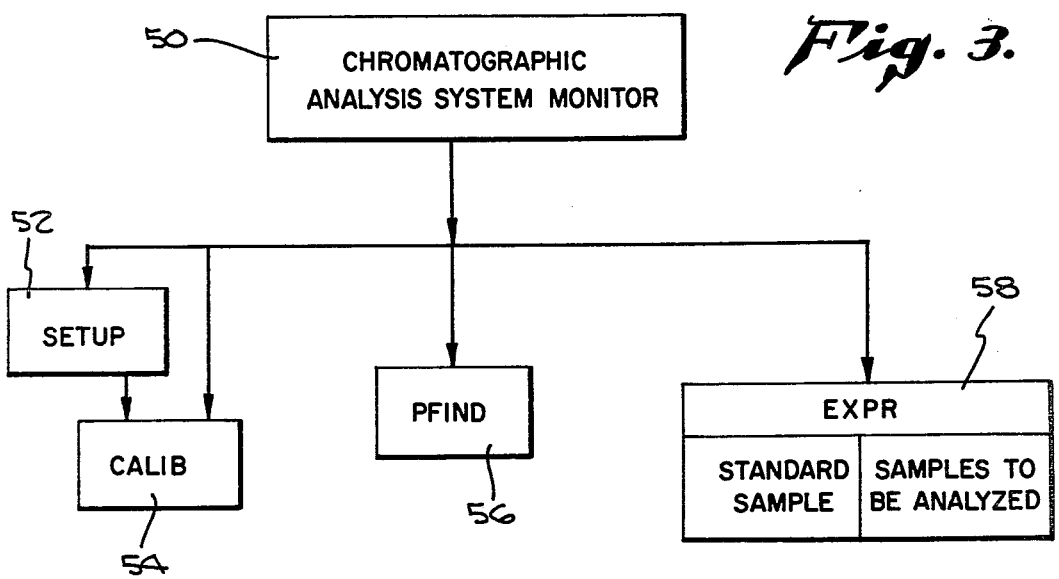
FIG. 3 is a block diagram of the major programs employed in the software portion of the system of the present invention.

All of the variables and I/O ports are initialized upon reset. Referring to FIG. 3, a monitor program 50 then waits for the user command entry from the terminal 48 to select the desired program function. There are four main programs as shown in the block diagram of FIG. 3. The program "SETUP" 52 is run at the beginning of a new experiment analysis. It sets up the experiment parameters and performs a calibration of the analog circuitry using the "CALIB" program 54. This verifies the operation and calibrates the analog-to-digital data conversion circuitry. The program "PFIND" 56 searches for peaks and estimates the retention time and peak width for all the peaks presented between the start time and final time specified by the operator. "EXPR" 58 is the main operating program which performs the data acquisition and peak size analysis for each sample using a digital filter. It is automatically rerun after each sample unless instructed to the contrary by the user.

The digital filter, to be described hereinafter, requires that a large number of mathematical operations be performed on floating point numbers. If it were applied to the chromatographic data continuously, the microprocessor 12 would be overwhelmed by the mathematical operations and could not keep pace with the data collected. The solution to successful data handling under such conditions is to specify a certain time window during which the chromatographic analysis system is to search for and measure each chromatographic peak. The shape of the filter is pre-established as the second differential of a Gaussian and scaled by the estimated half-height peak width. At the beginning of the experiment, the "SETUP" program 52 queries the user to determine the number of chromatographic peaks to be analyzed, the estimated retention time and width of each peak, and the internal standard peak on which the ratios of the relative peak sizes are computed.

The analog hardware is tested and calibrated by the program "CALIB" 54 which follows automaticalldy after "SETUP" 52. The data acquisition hardware is placed in the calibration mode, and the calibration voltage is connected in place of the chromatographic signal input. With the autoranging capability disabled, the hardware steps through the calibration signal multiplexer and performs an analog-to-digital conversion on each integrator 24, 26, 28. The binary bits of each conversion are taken in by the data acquisition interrupt-handling subroutine and stored in microprocessor memory. With the integrator inputs connected to 0 volts, the offset voltages are measured. By applying the offset and gain conversion factors to the data acquired in the autoranging mode, a linear and precise dynamic range of 110 dB can be achieved. The "CALIB" program 54 can also be called by the user at any time to assure the proper operation of the data acquisition hardware.

The data acquisition routine is invoked by a "data-ready" interrupt request from the hardware. Data are taken in from the analog-to-digital converter 14 each time an end-of-conversion interrupt is received from gate 46 between the start time and stop time from the "SETUP" program 52. A data saturation check is performed inside this routine to alert the user of full scale digital word from the analog-to-digital conversion system. Data acquisition can be terminated by pushing an "ABORT" button which is interrogated by the data acquisition routine. When operating in the "CALIB" mode, the routine takes in binary words and stores them sequentially in memory. When operating in normal mode during "EXPR" 58 of "PFIND" 56, the binary words taken in are subtracted from the offset bits and then multiplied by the gain factor associated with the corresponding integrator from which the conversion was performed. The corrected number thus derived is in units of volts and expressed as a 32-bit floating point number. The analog sampling rate is fixed by the hardware clock at 10 sec$^{-1}$. The data acquisition routine collapses a predetermined number of sample points into one data point, and stores it in a circular queue of 2-kbyte capacity (512 data points), for use by the analysis routine. The sample points are collapsed to provide a minimum of six data points across the half-height width of the first chromatographic peak.

The system of the present invention is unique in two interrelated regards. In prior art systems, each run is separate and neither learns nor uses anything derived from previous runs. Moreover, whether peak height measurement or peak area integration is utilized, the data is calculated with reference to the highly erratic and undependable baseline. The present system both "learns" particular characteristics of the apparatus doing the actual sampling and eliminates the use of the baseline. This is accomplished by using the prior knowledge that the data peaks are Gaussian in nature. Known data is then used to parameterize a curve fit filter to the components of interest in the apparatus in use. Thus, the filter first "learns" the characteristics of the system. As actual data is then sampled under unknown quantity conditions, the filter is employed to produce a "best fit" of the data peak curve independent of the baseline. From the filter is then derived a figure of merit reflecting the value of the unknown curve from which the quantity of the unknown component can be directly calculated.

Figure 5:
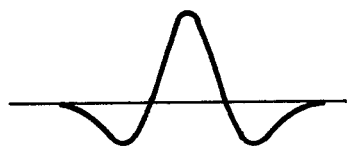
FIG. 5 is a curve representing the second differential of the Gaussian which is convolved with the data.

The actual filtering is done by using a finite impulse response filter with a length of 12$\sigma$ and the shape of a second differential Gaussian (see FIG. 5). The length of the filter is chosen to be 12$\sigma$ such that the value of the filter function for $|x|>6\sigma$ is less than $-10^{-6}$. The filter function is expressed as follows:

$$f(x) = \left(\frac{2}{\sigma}\right)^{3/2} \left(1 - \frac{x^2}{\sigma^2}\right) e^{-\frac{x^2}{2\sigma^2}} \qquad (I)$$

Figure 4:
FIG. 4 is a Gaussian curve representing the approximate shape of a chromatographic peak.
Figure 6:
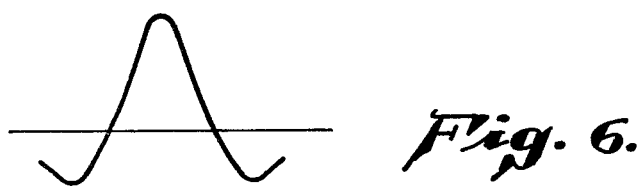
FIG. 6 is a curve representing the shape of the data.
Figure 7:
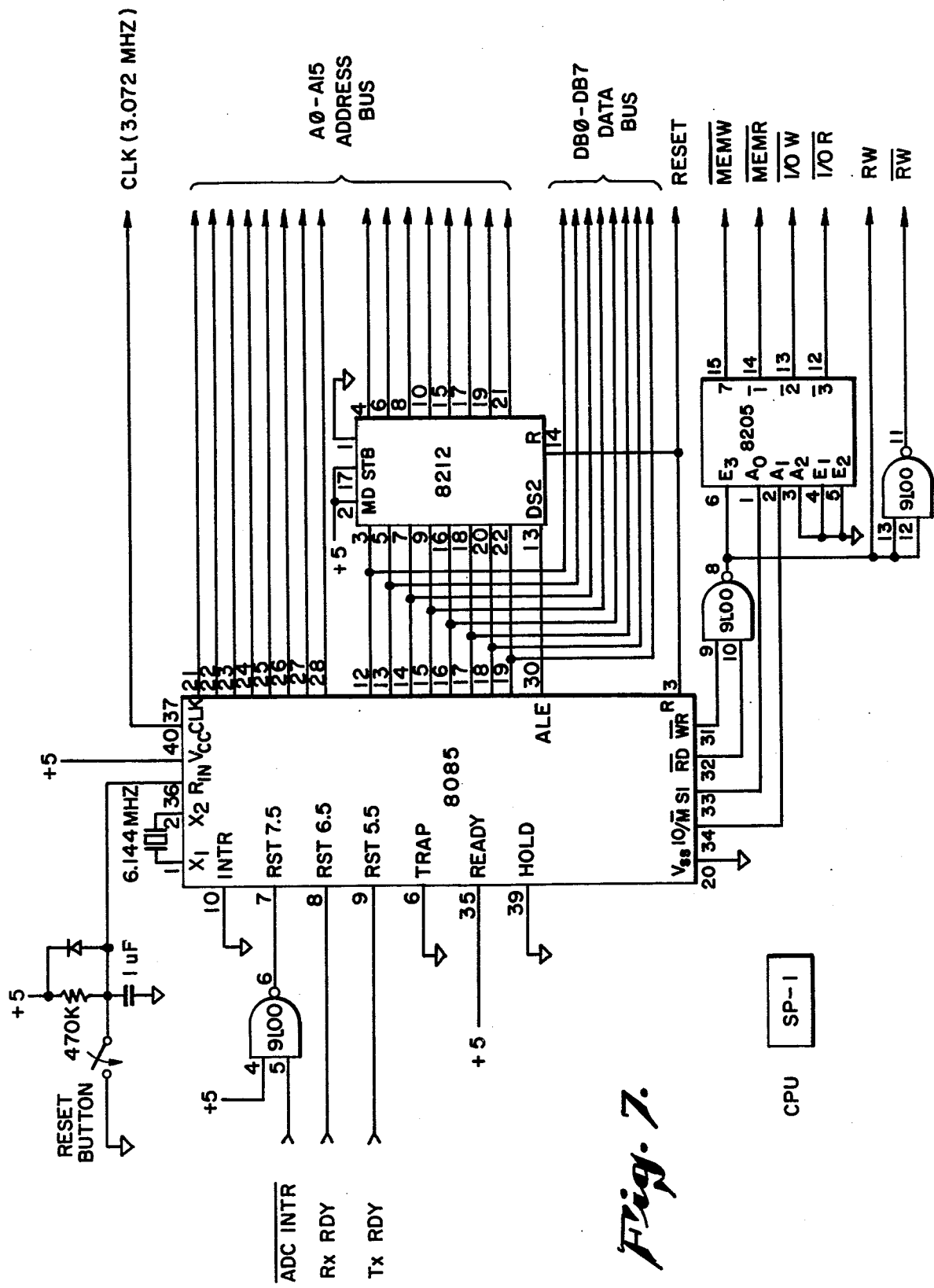
FIGS. 7-18 are block circuit diagrams setting forth the computational portion of the system of the present invention.
Figure 8:
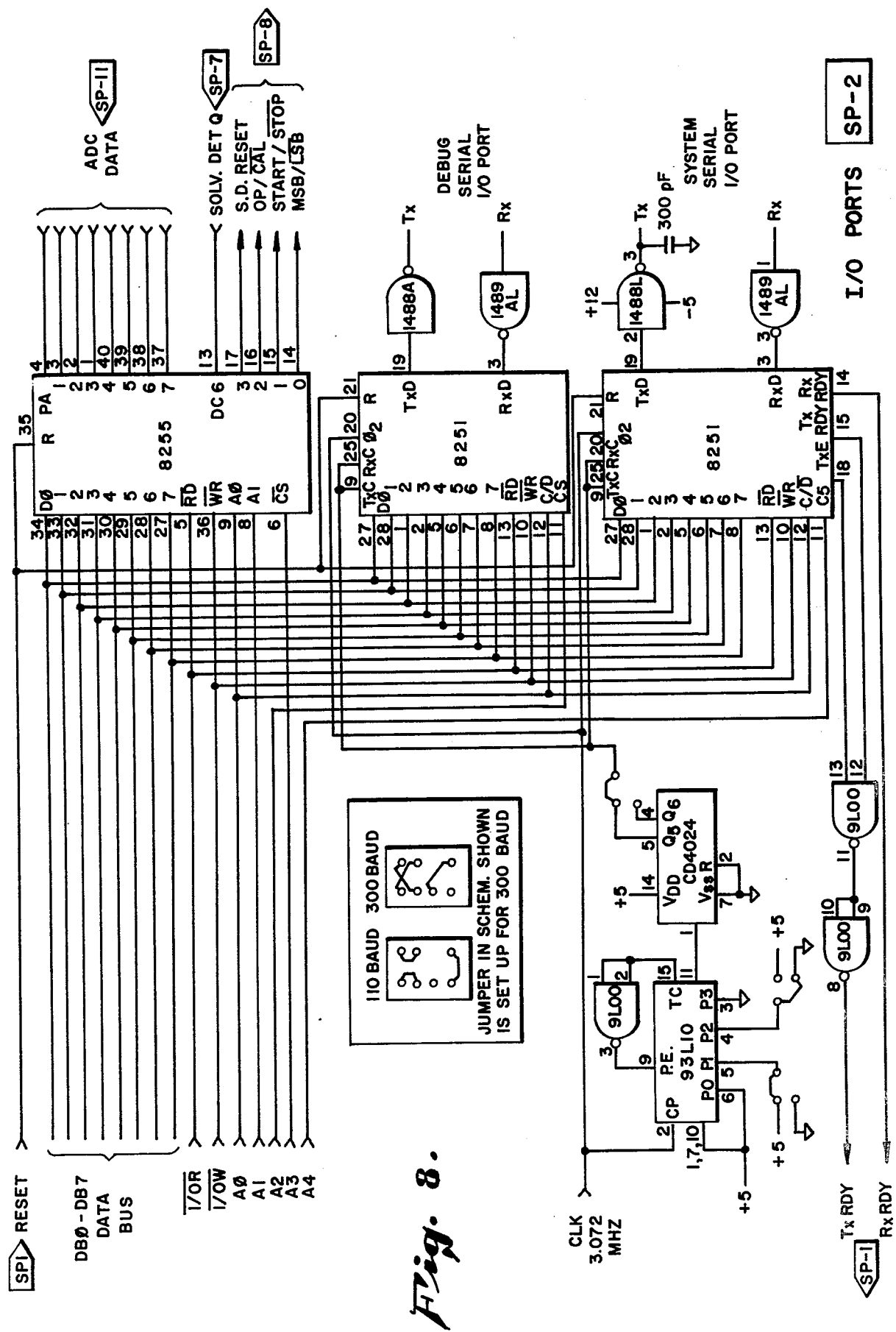
Figure 9:
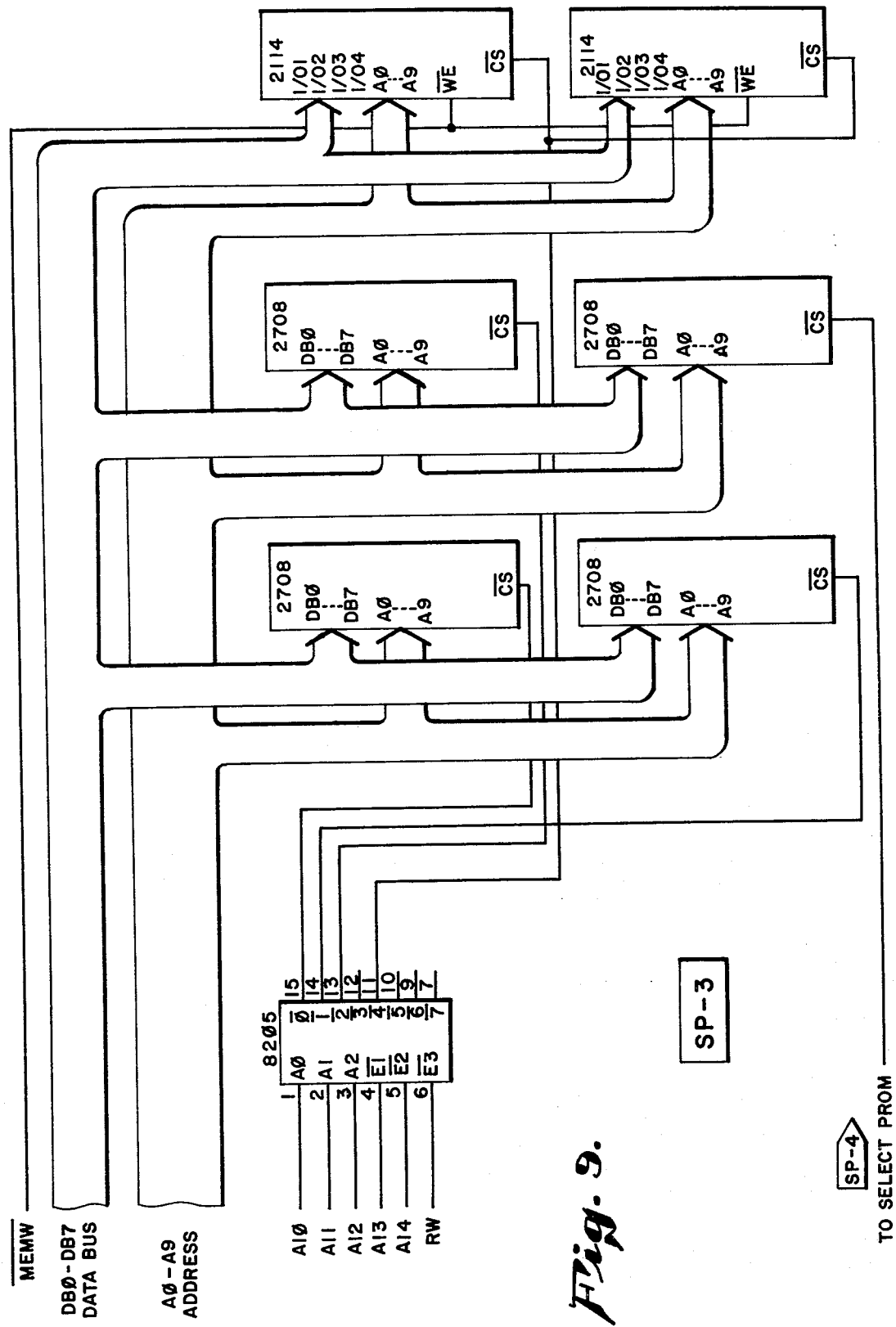
Figure 10:
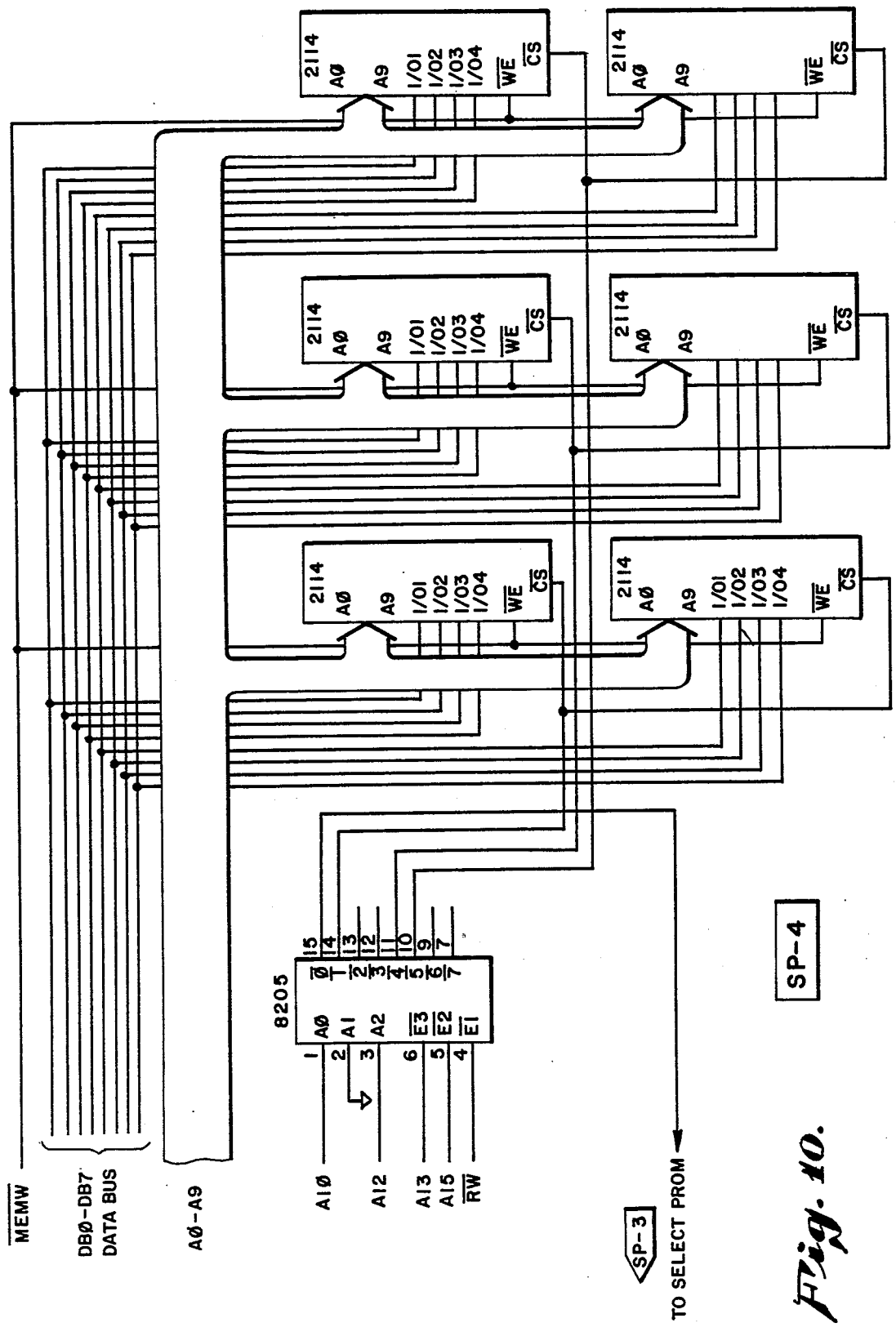
Figure 11:
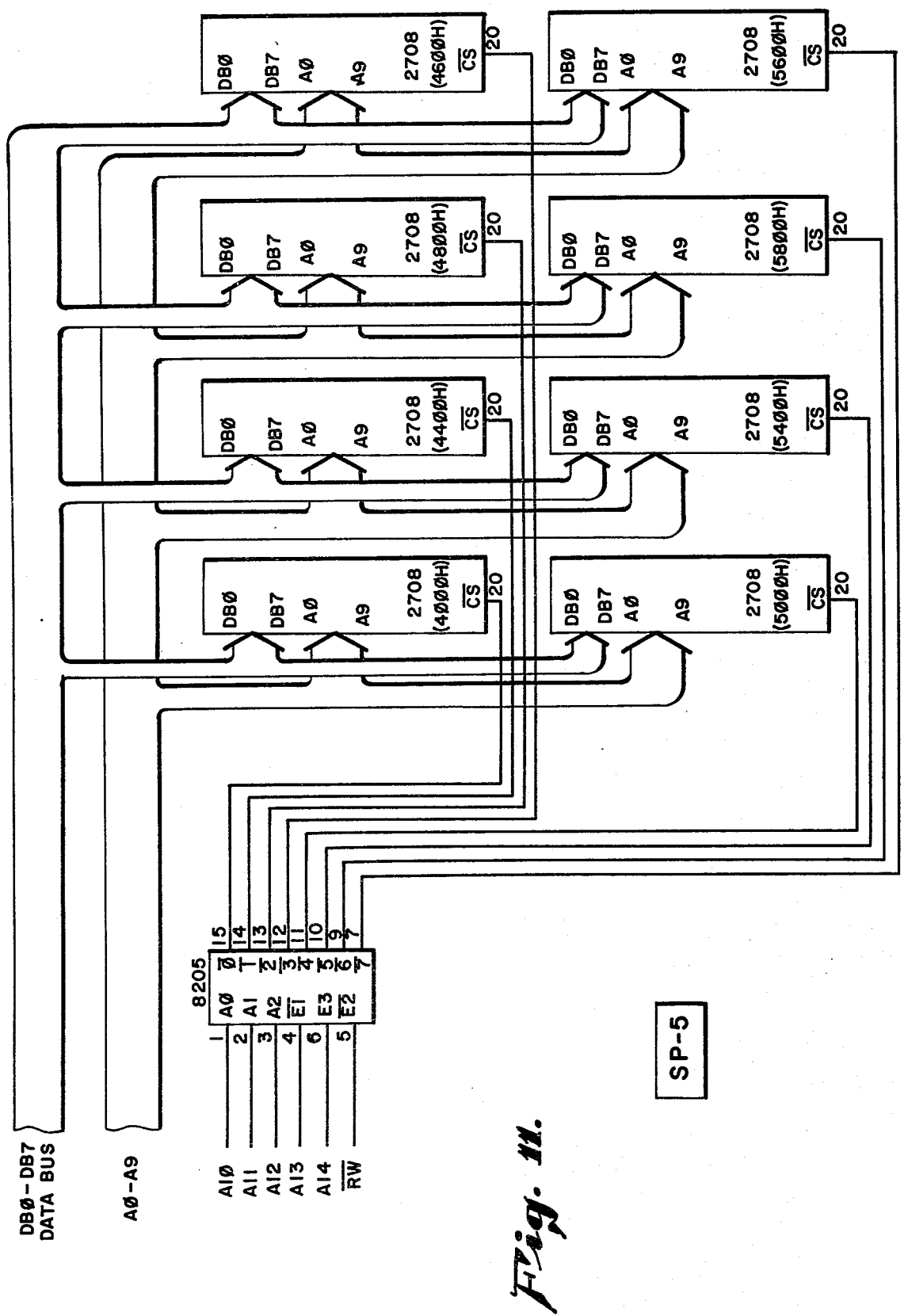
Figure 12:
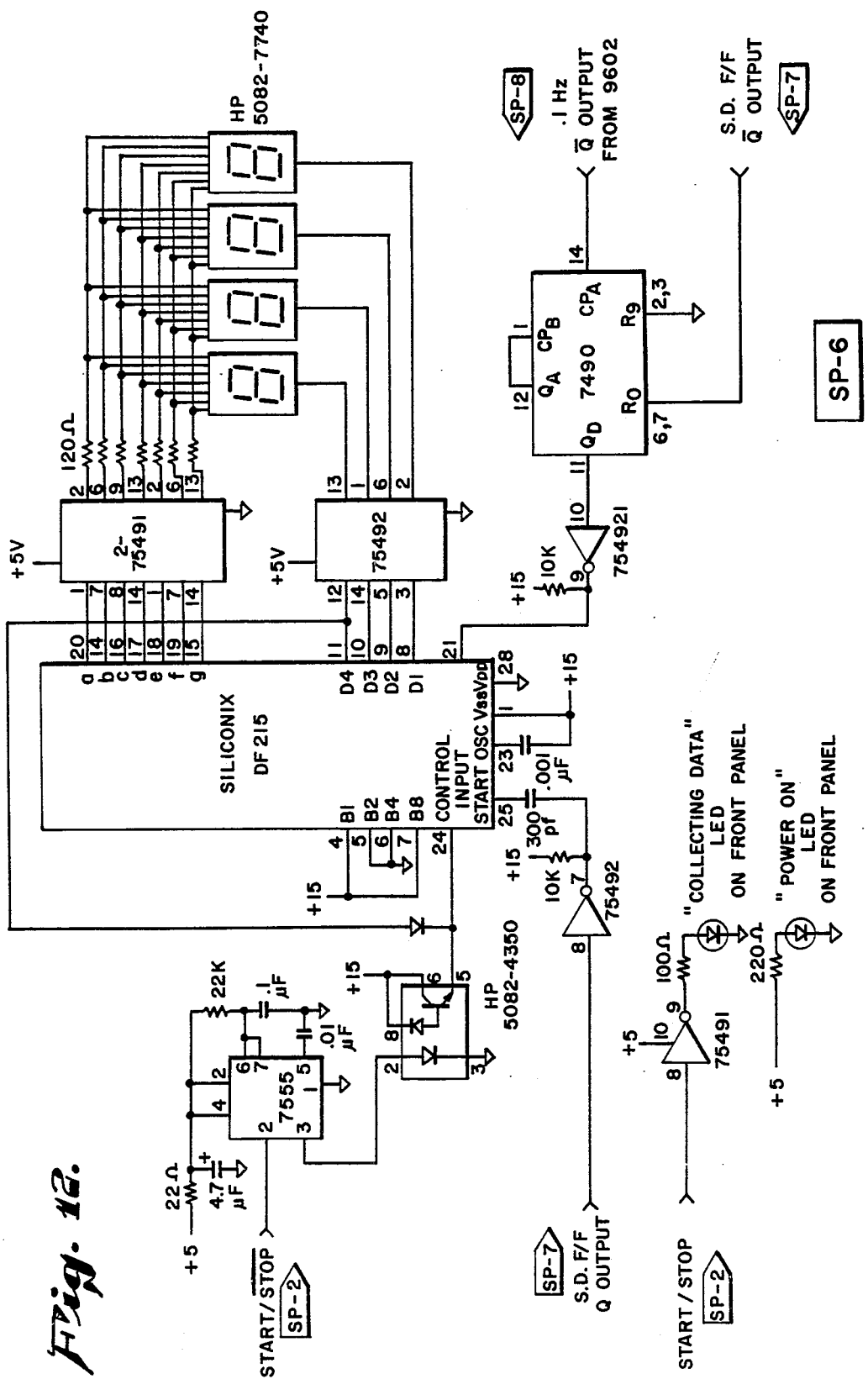
Figure 13:
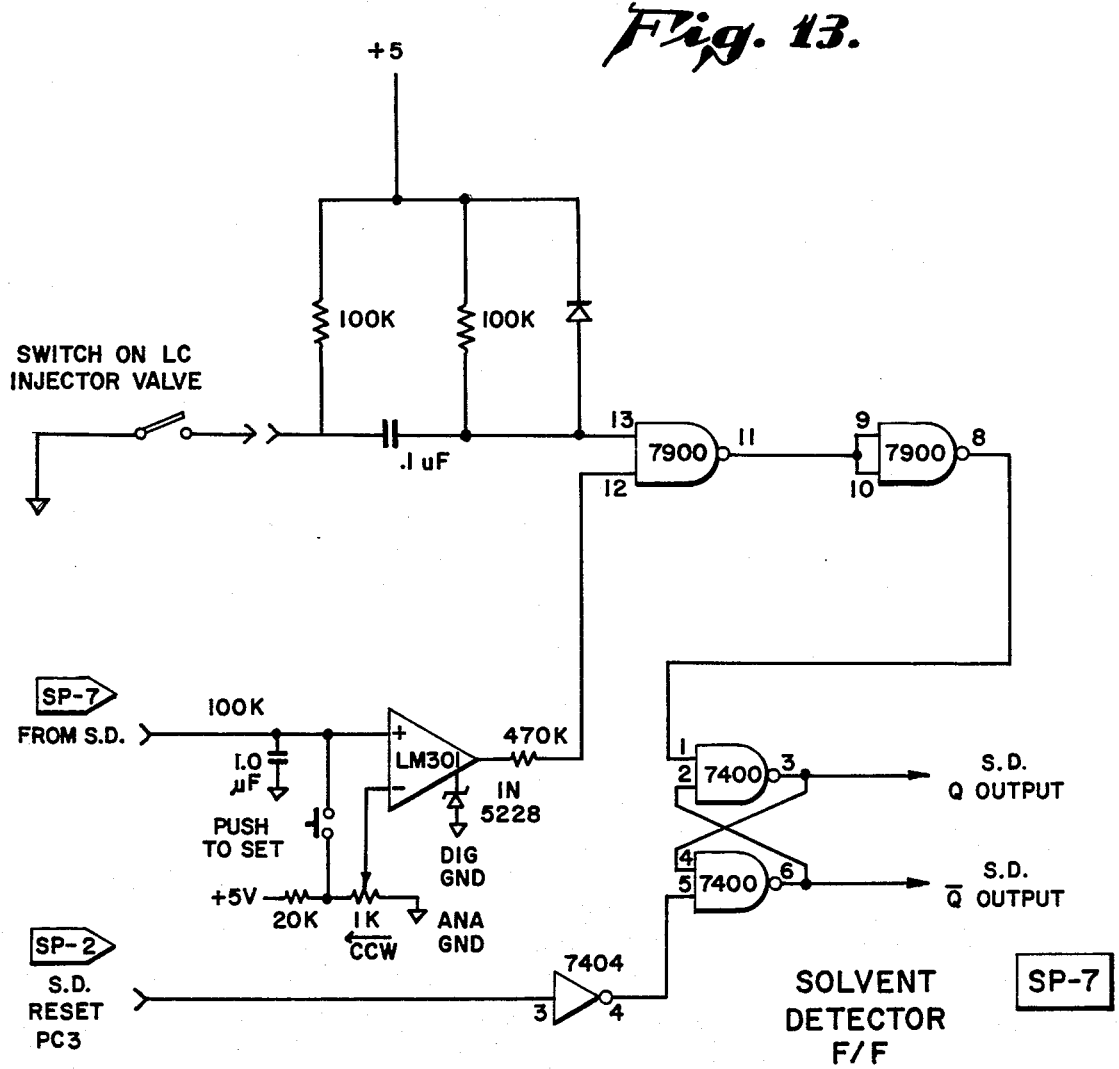
Figure 14:
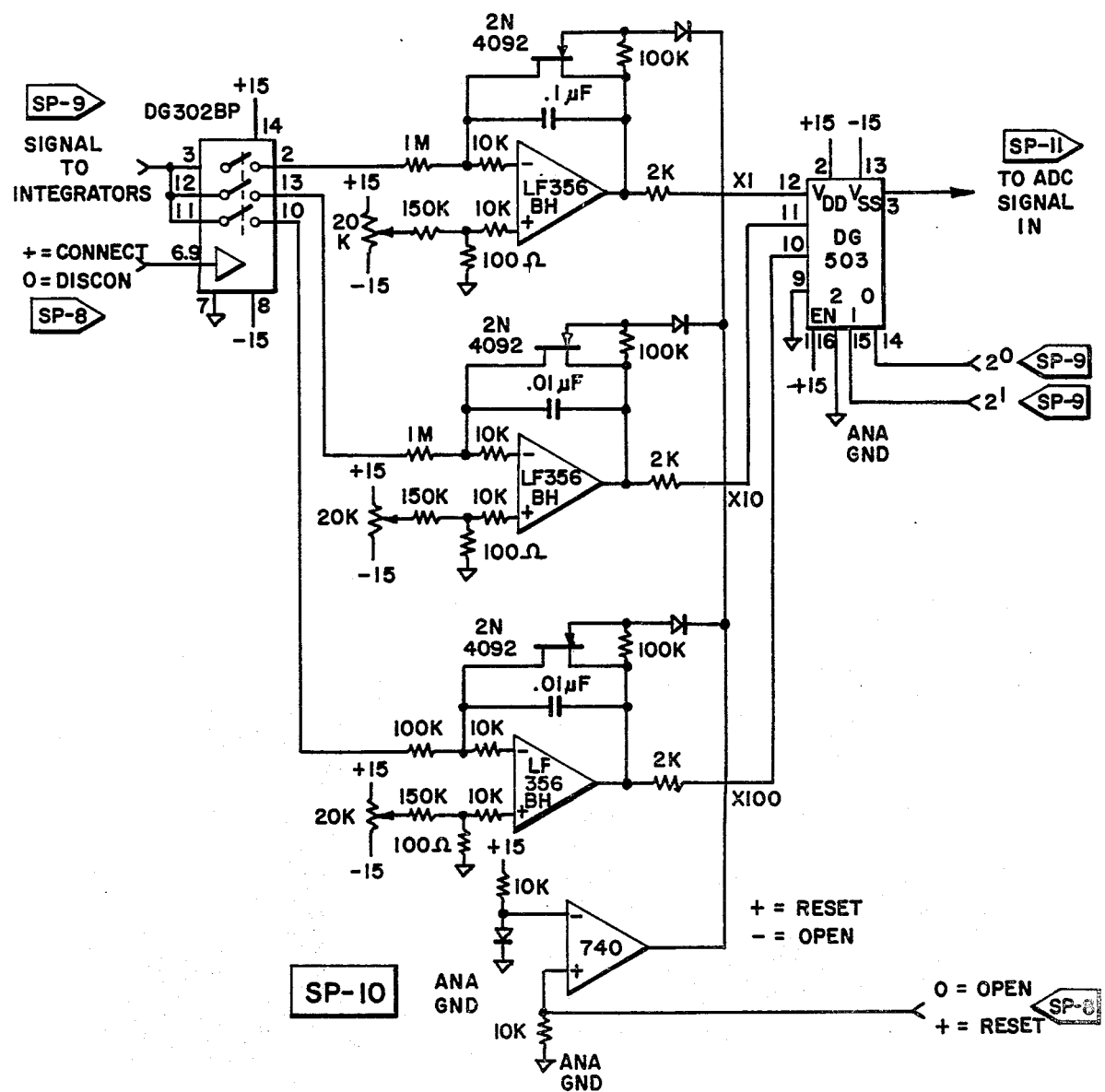
Figure 15:
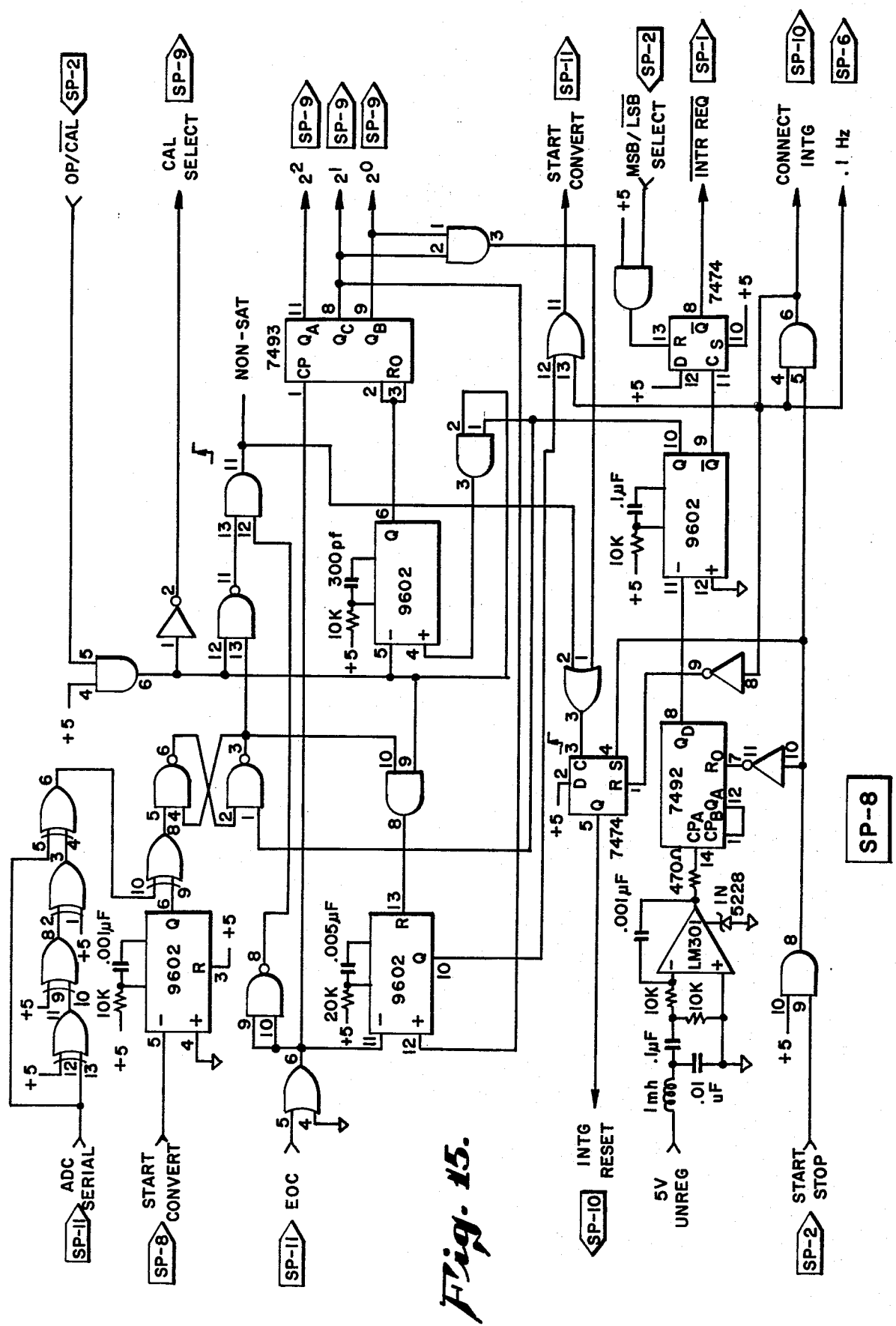
Figure 16:
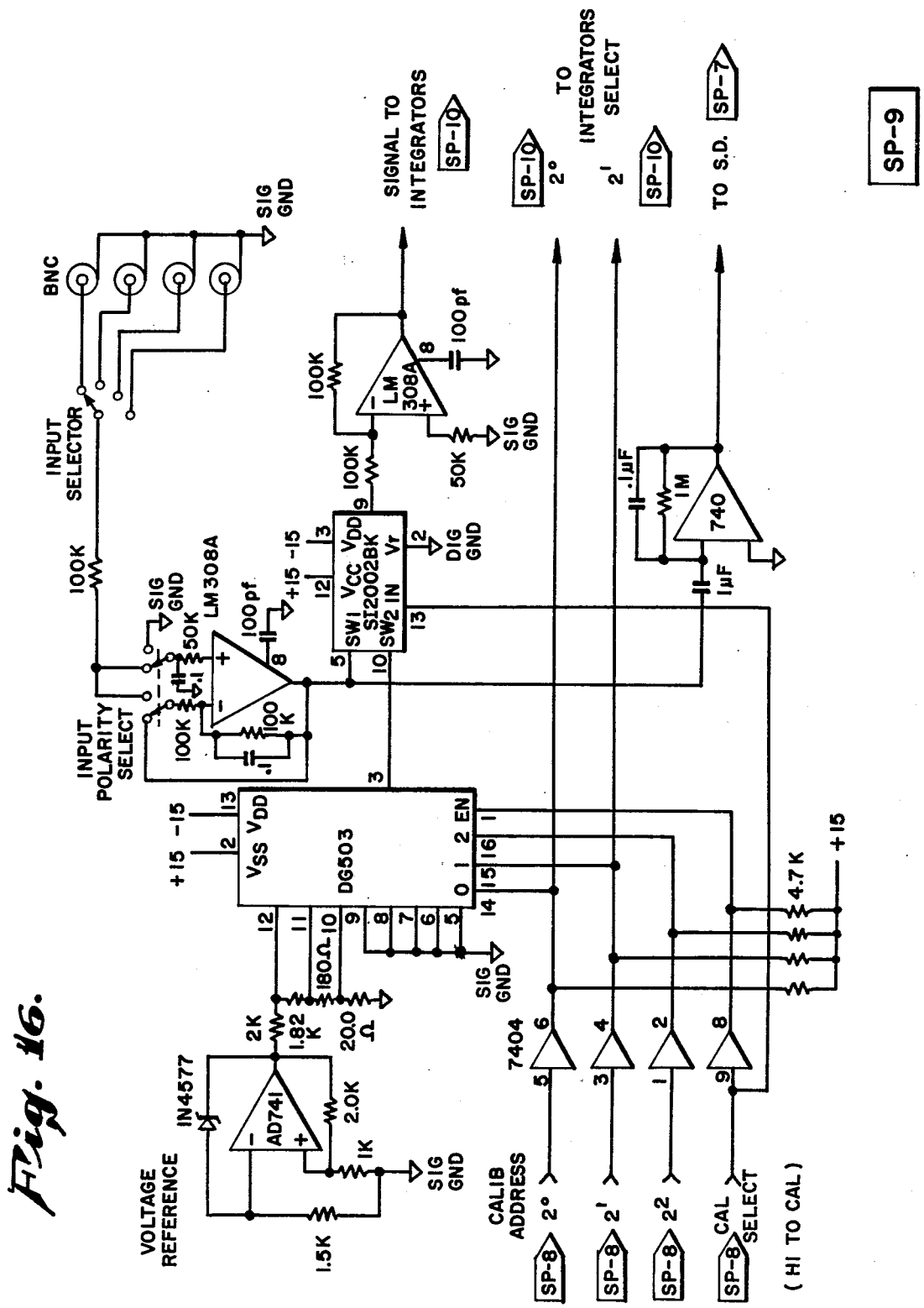
Figure 17:
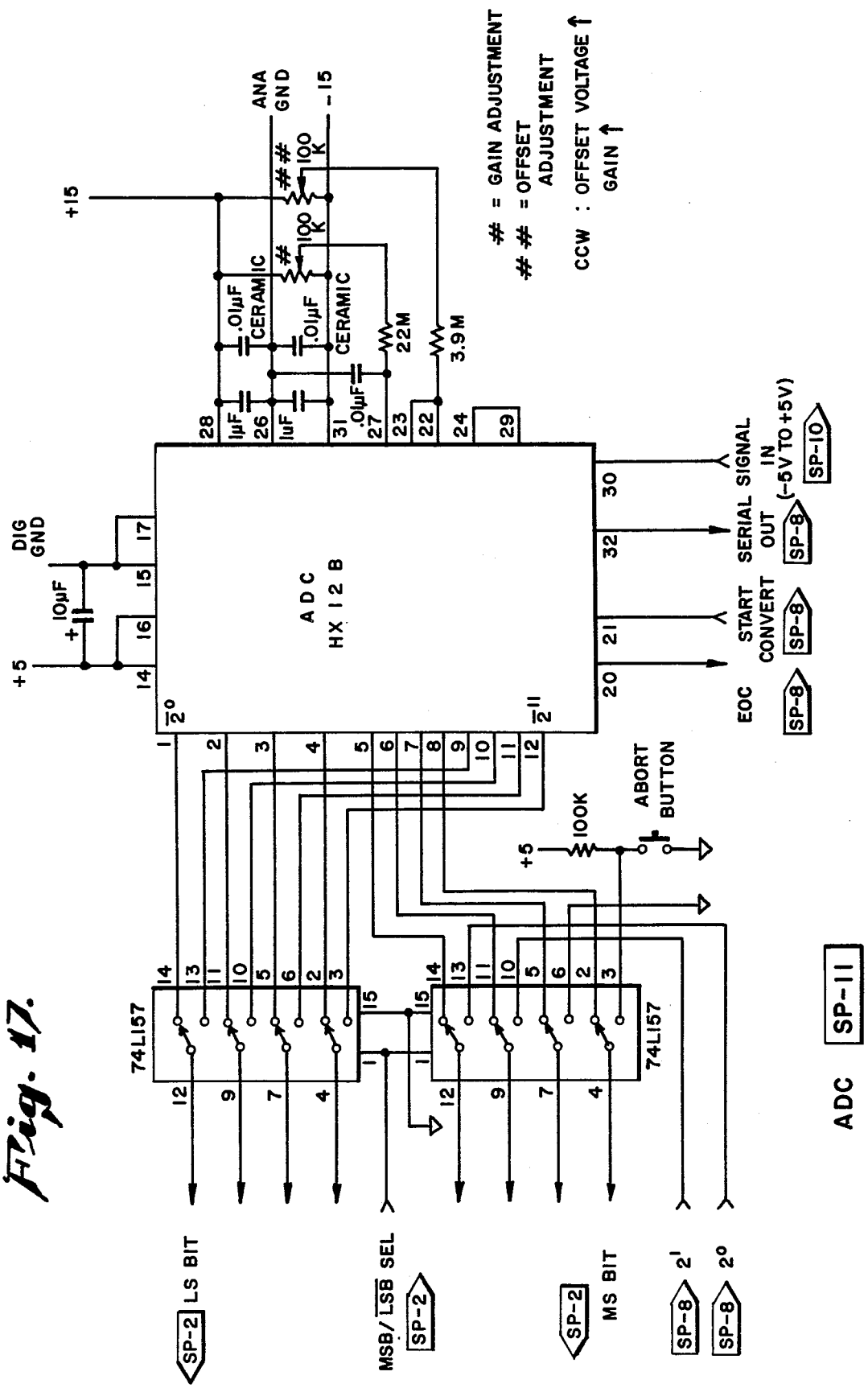
Figure 18:
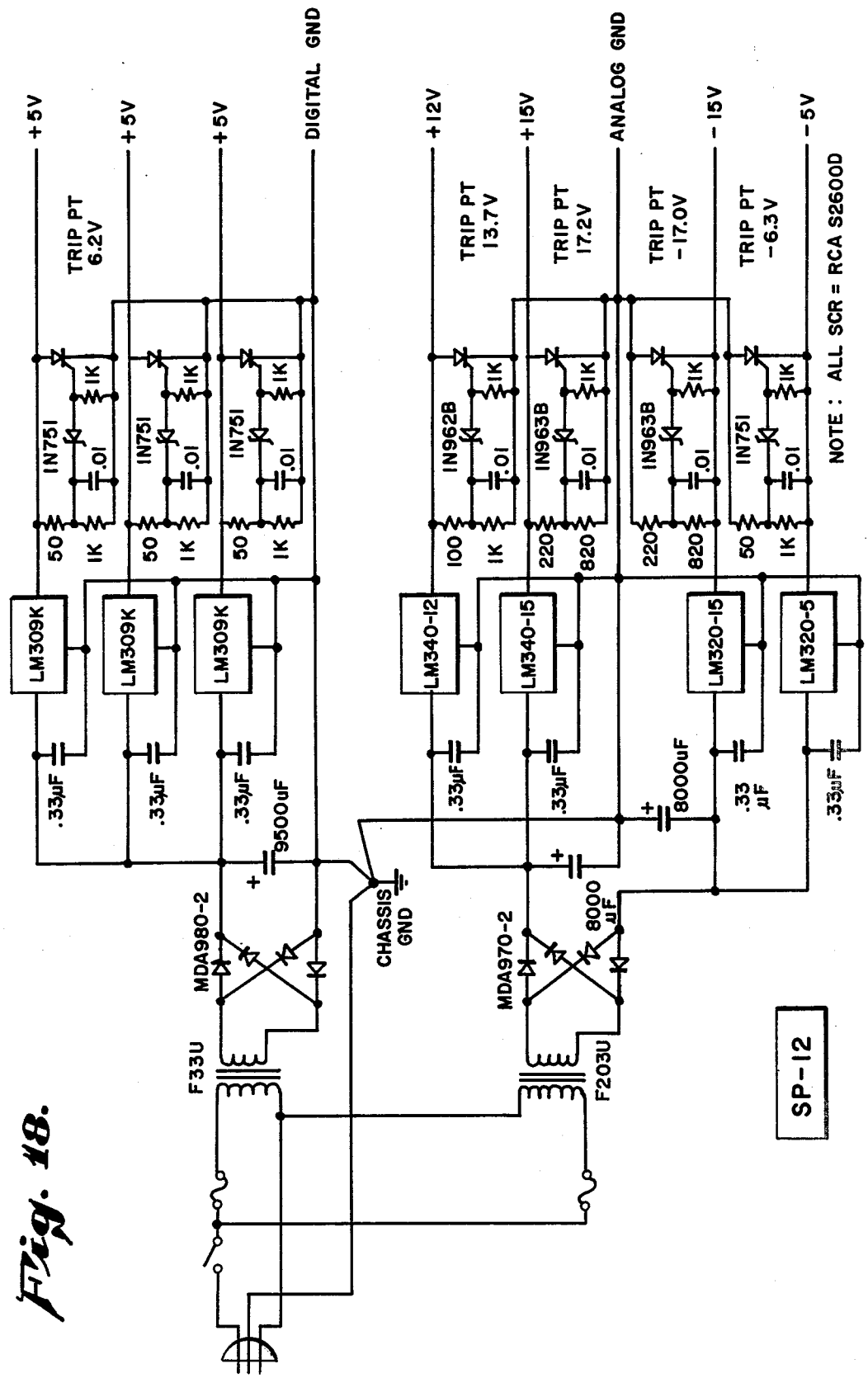
Figure 19:
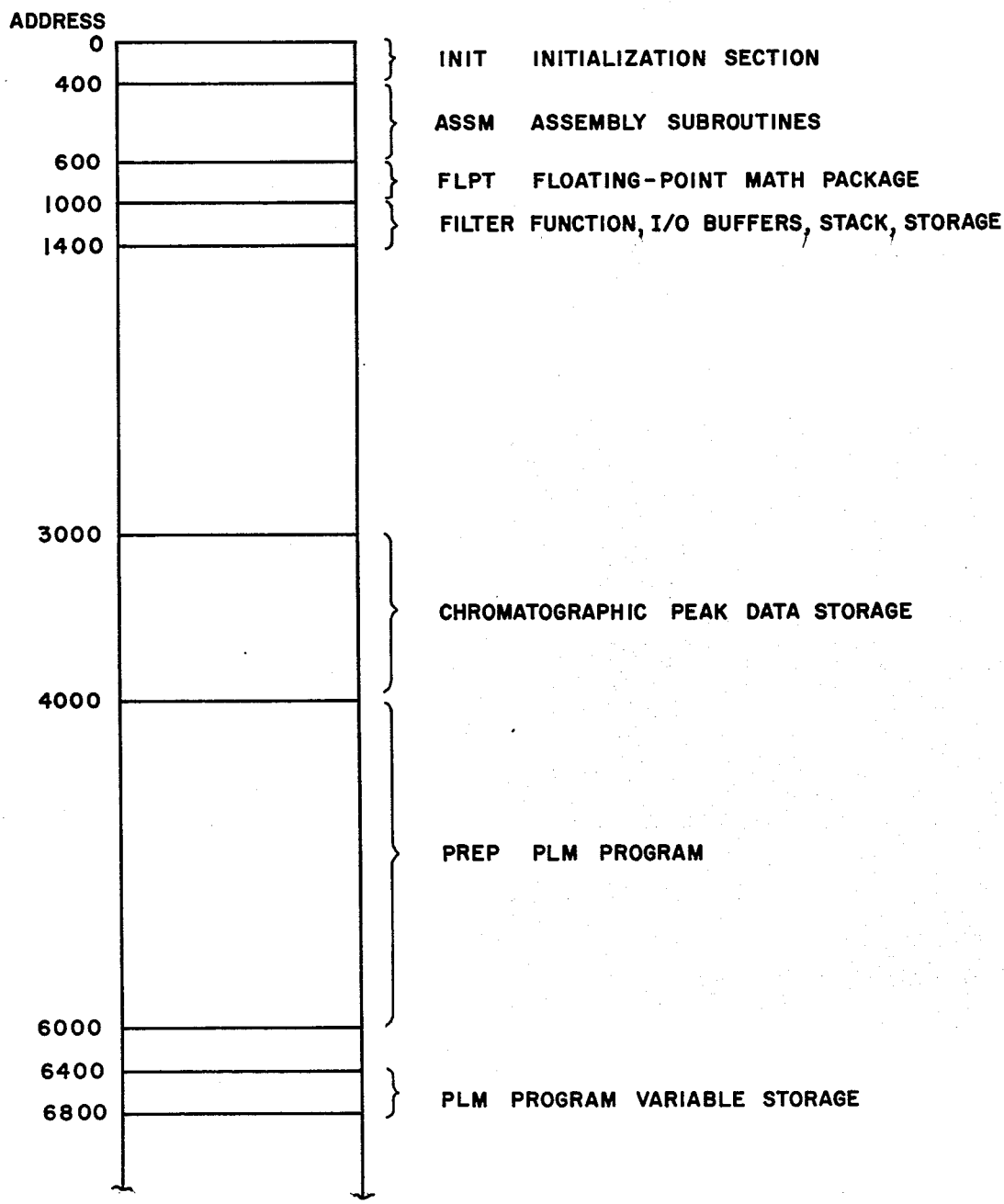
FIGS. 19-29 are flowcharts of the software programs employed in the system of the present invention for practicing the method thereof.
Figure 20:
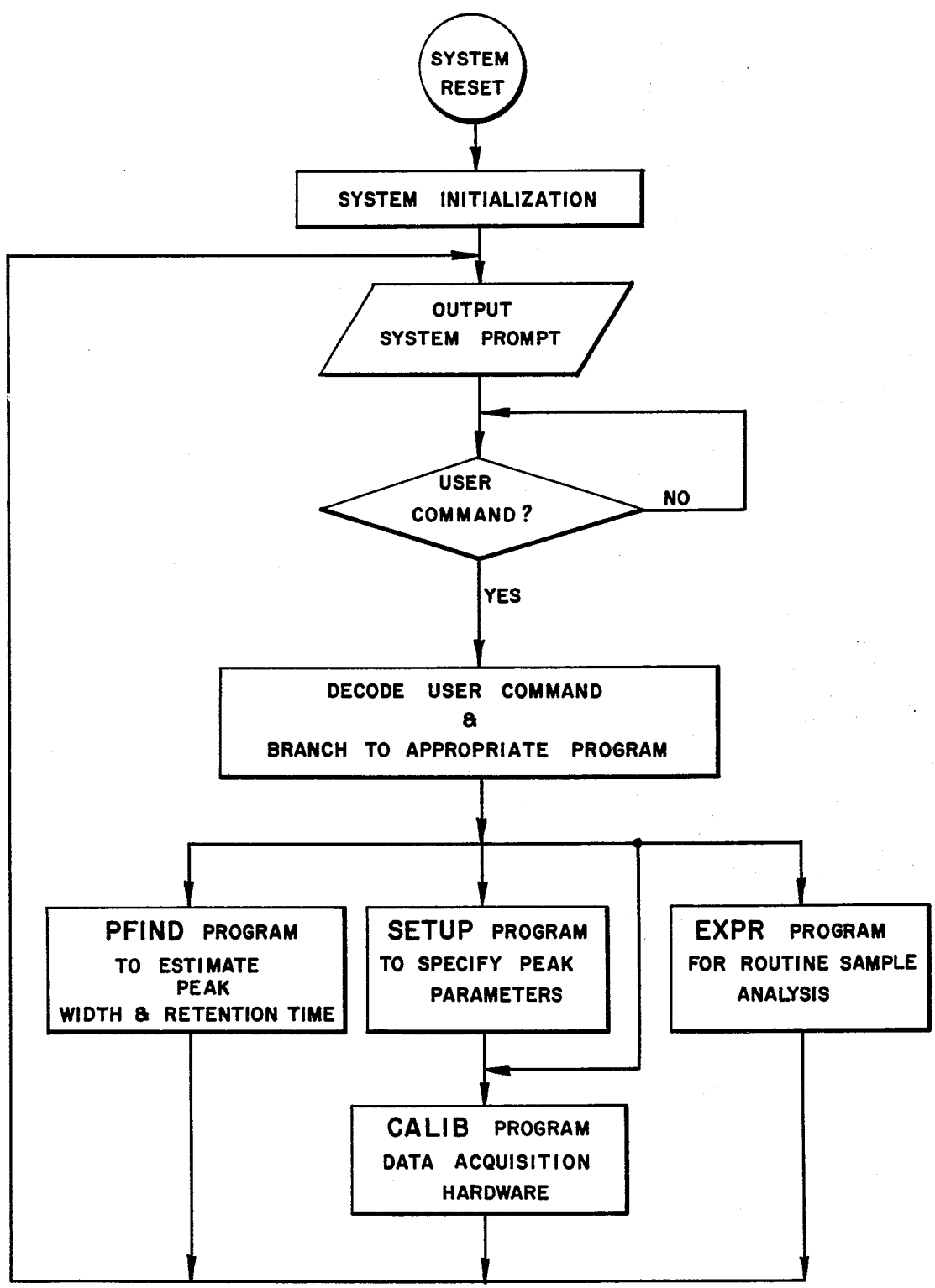
Figure 21:
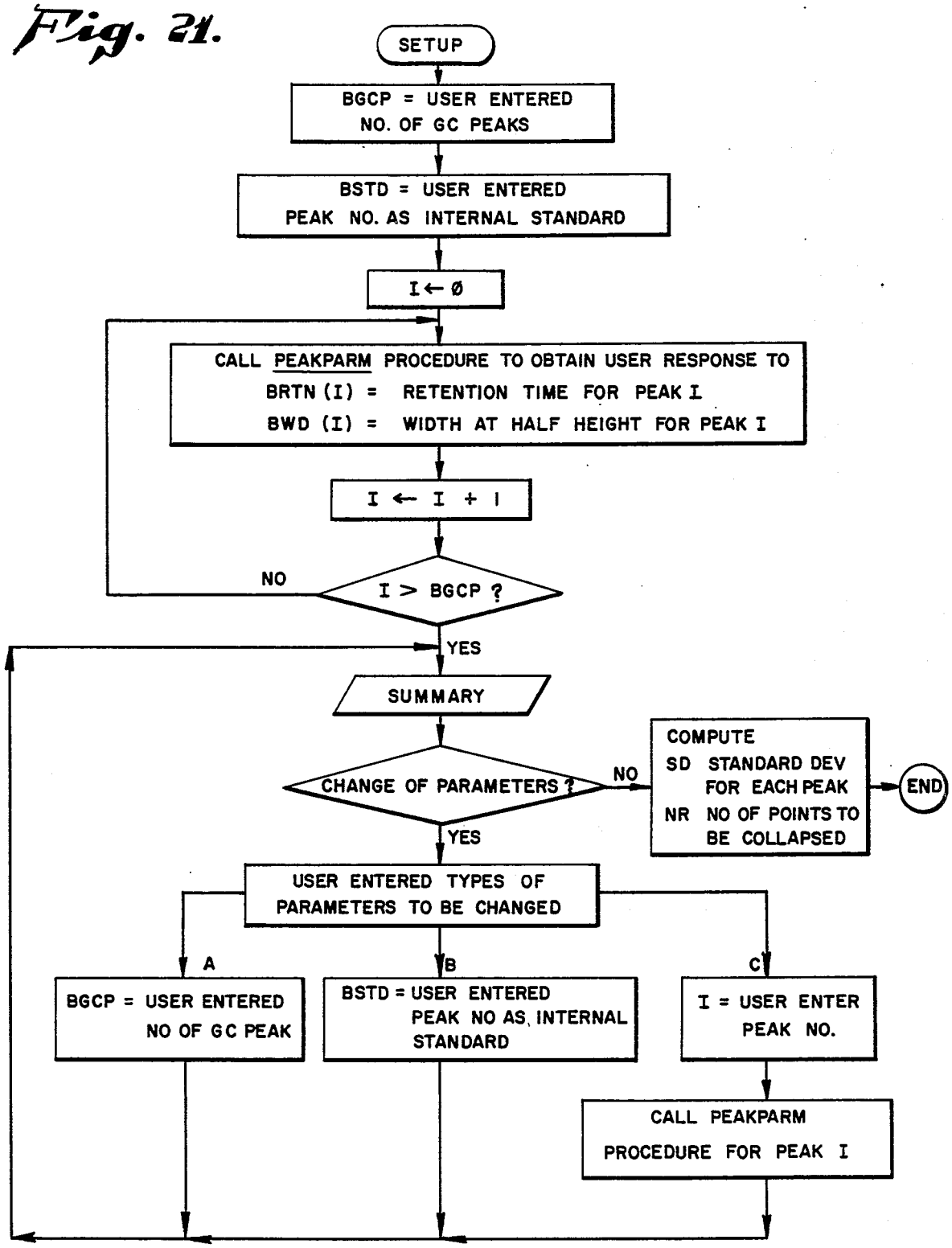
Figure 22:
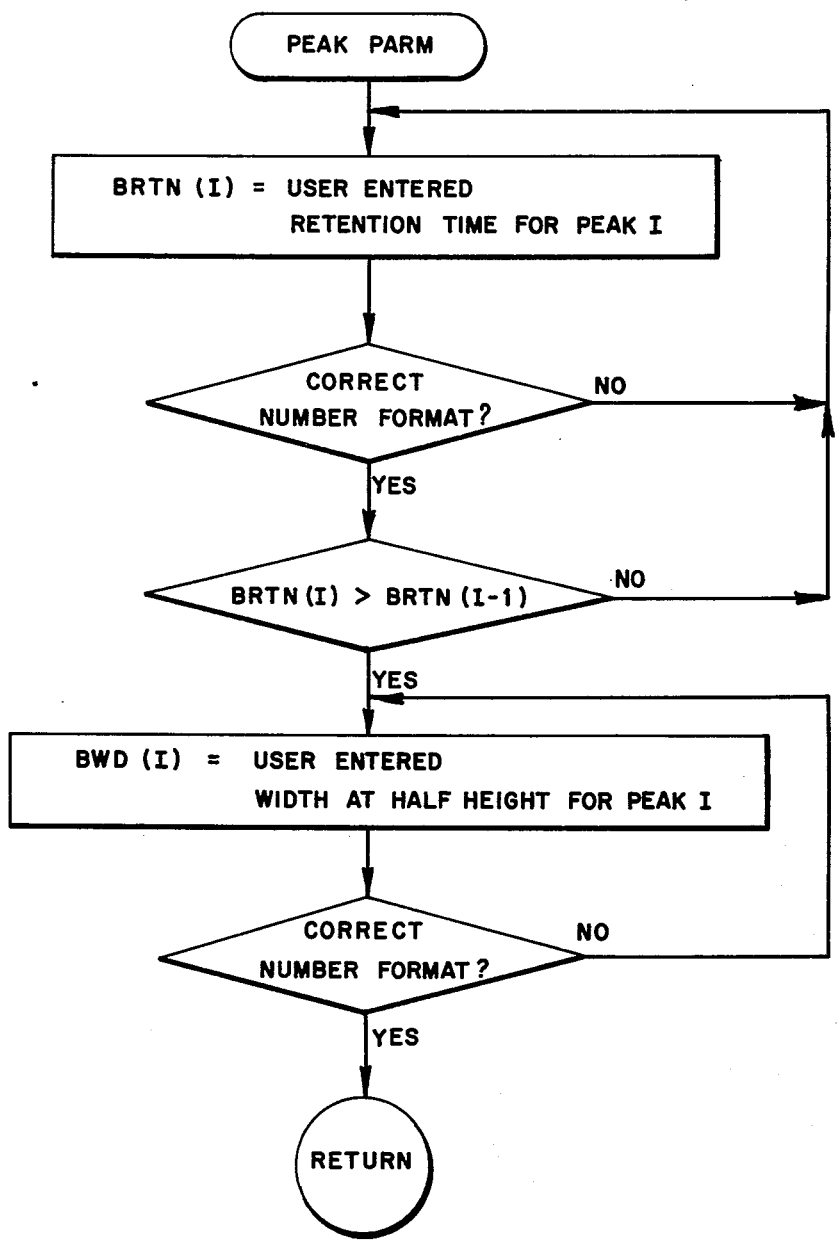
Figure 23:
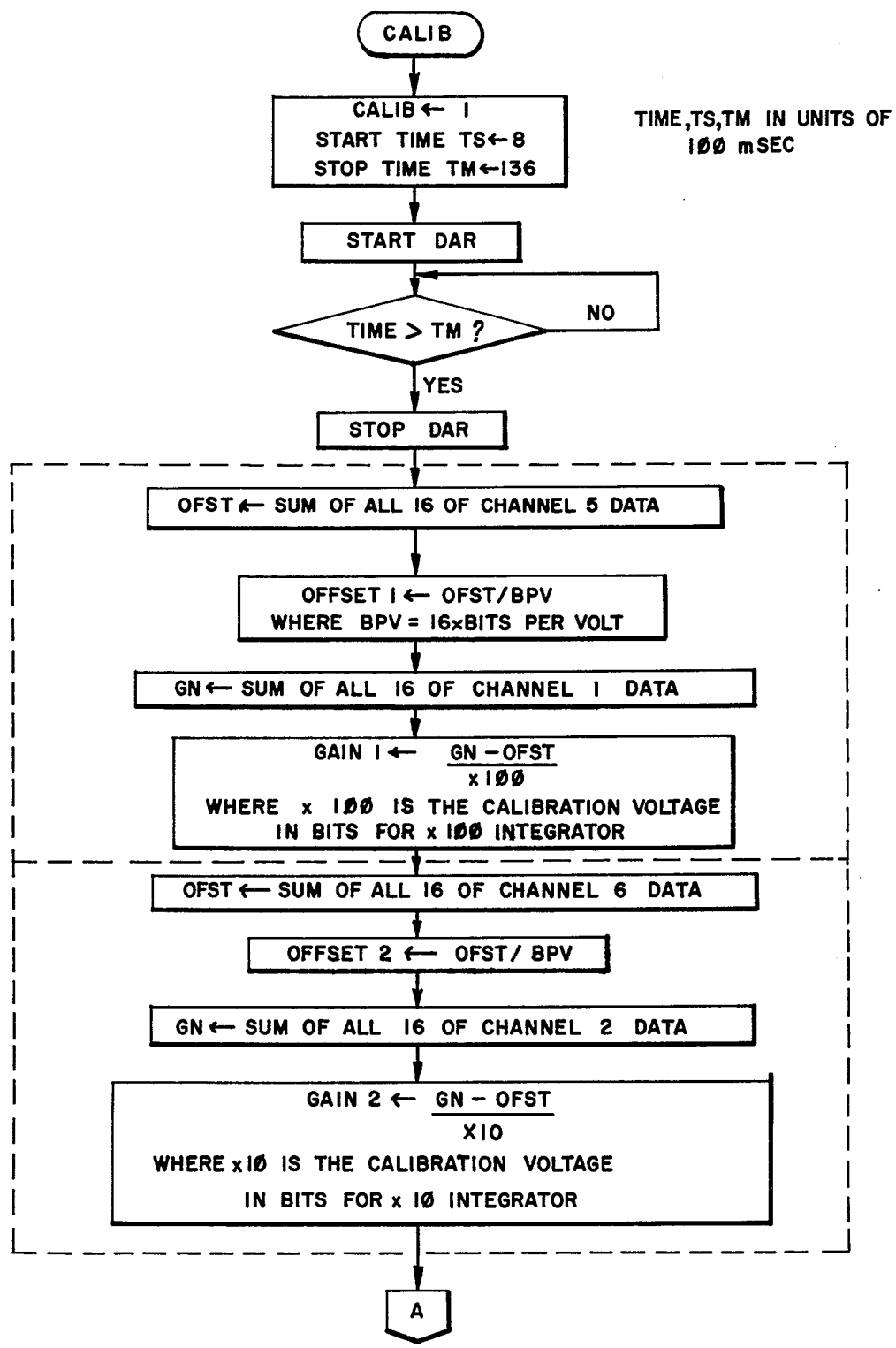
Figure 23:
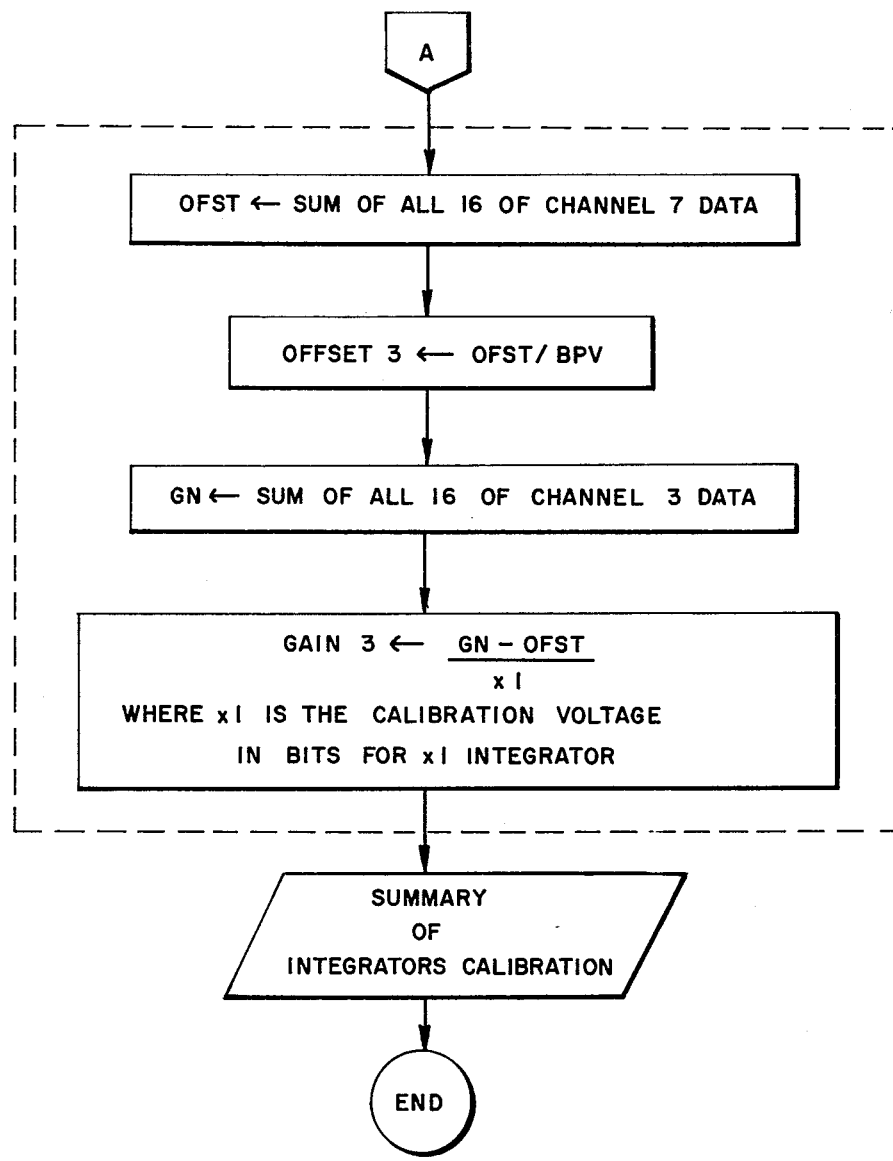
Figure 24:
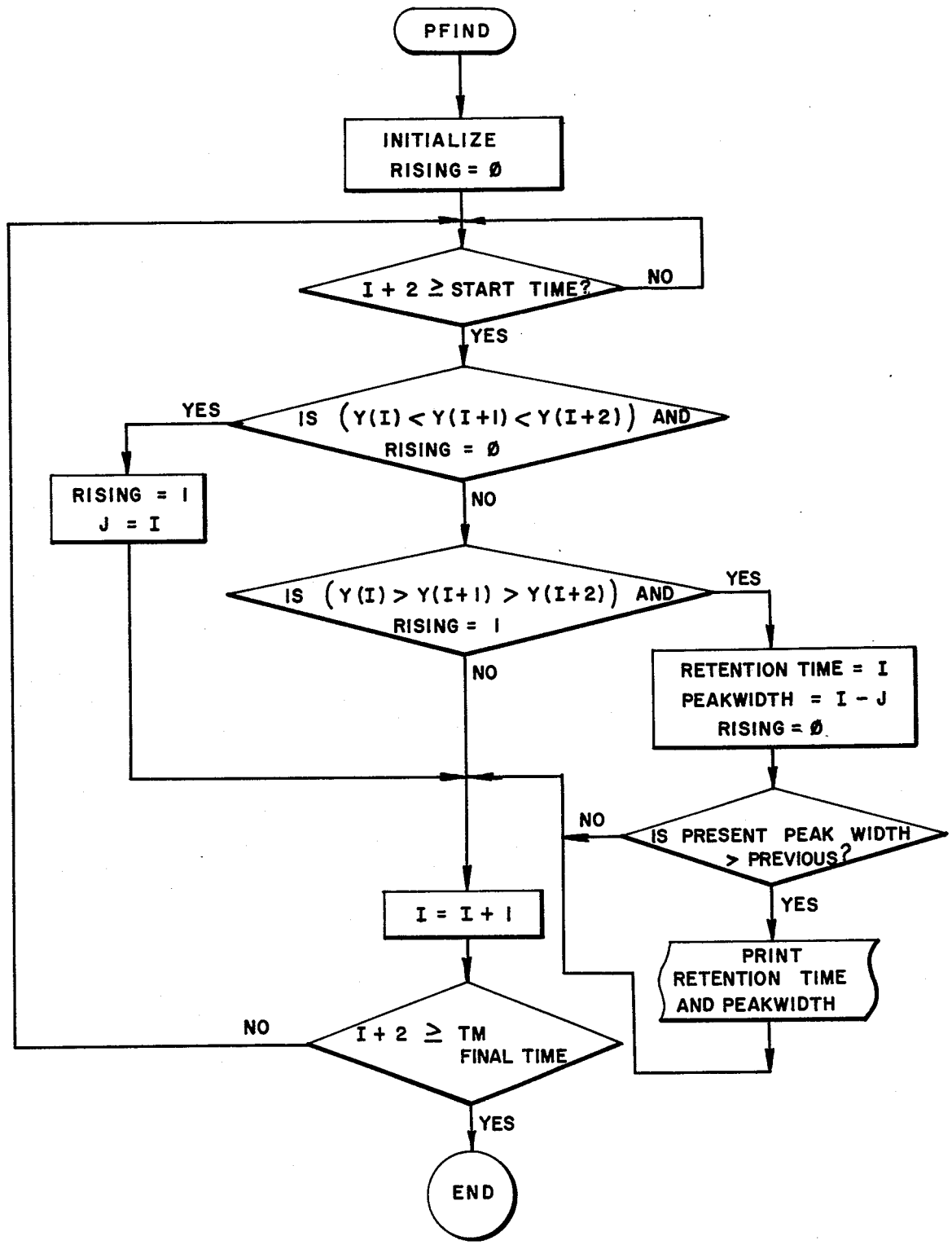
Figure 25:
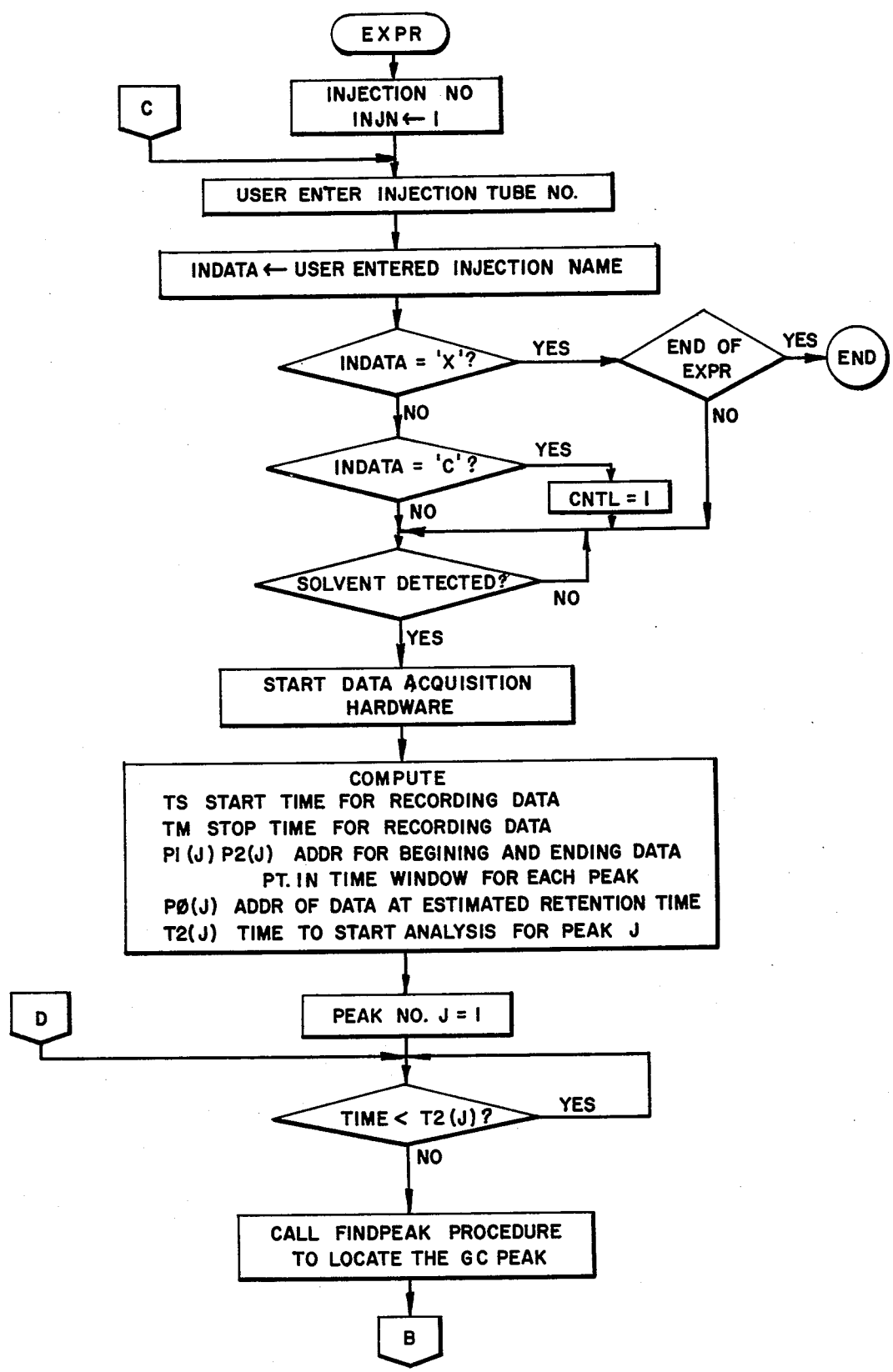
Figure 25:
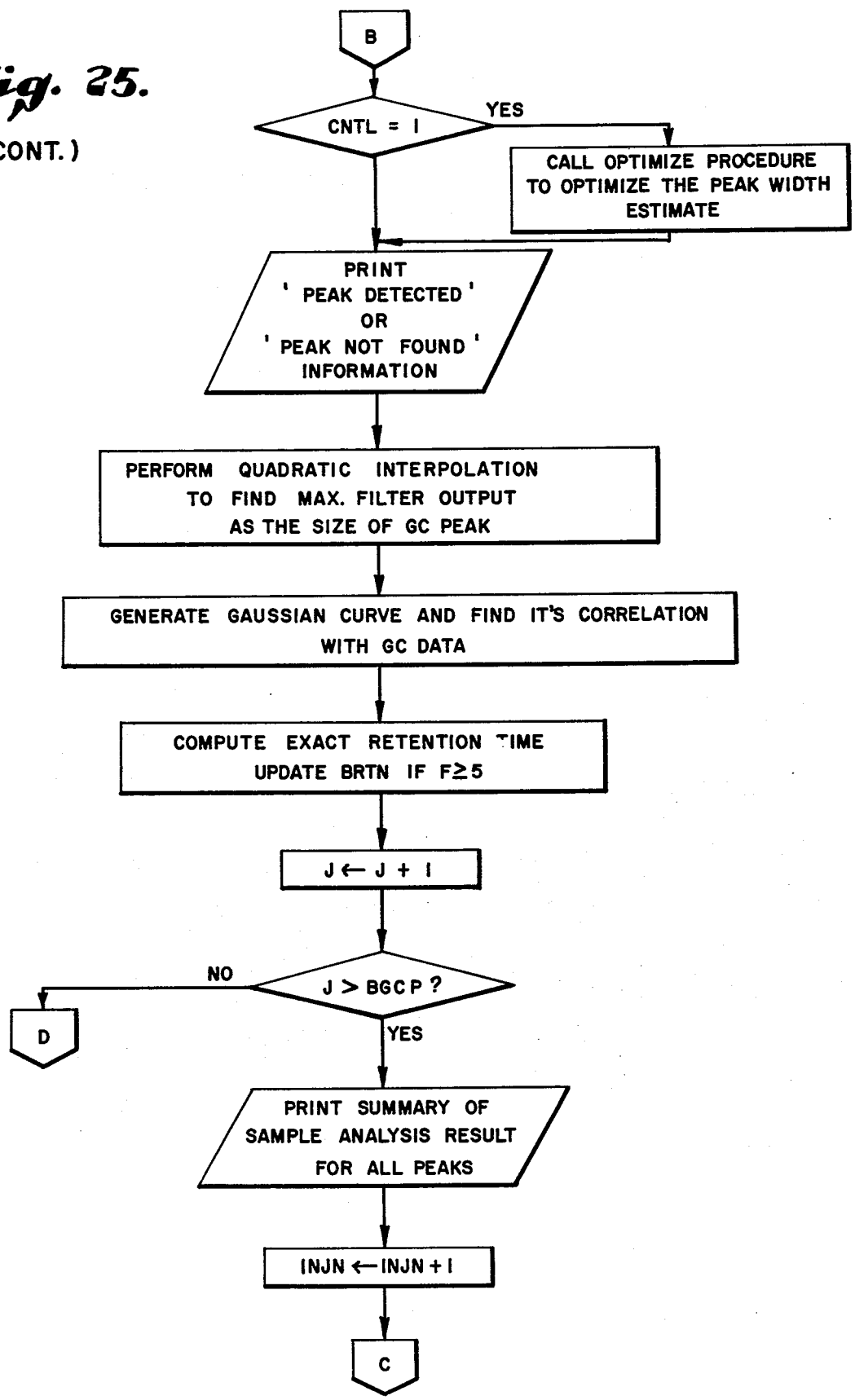
Figure 26:
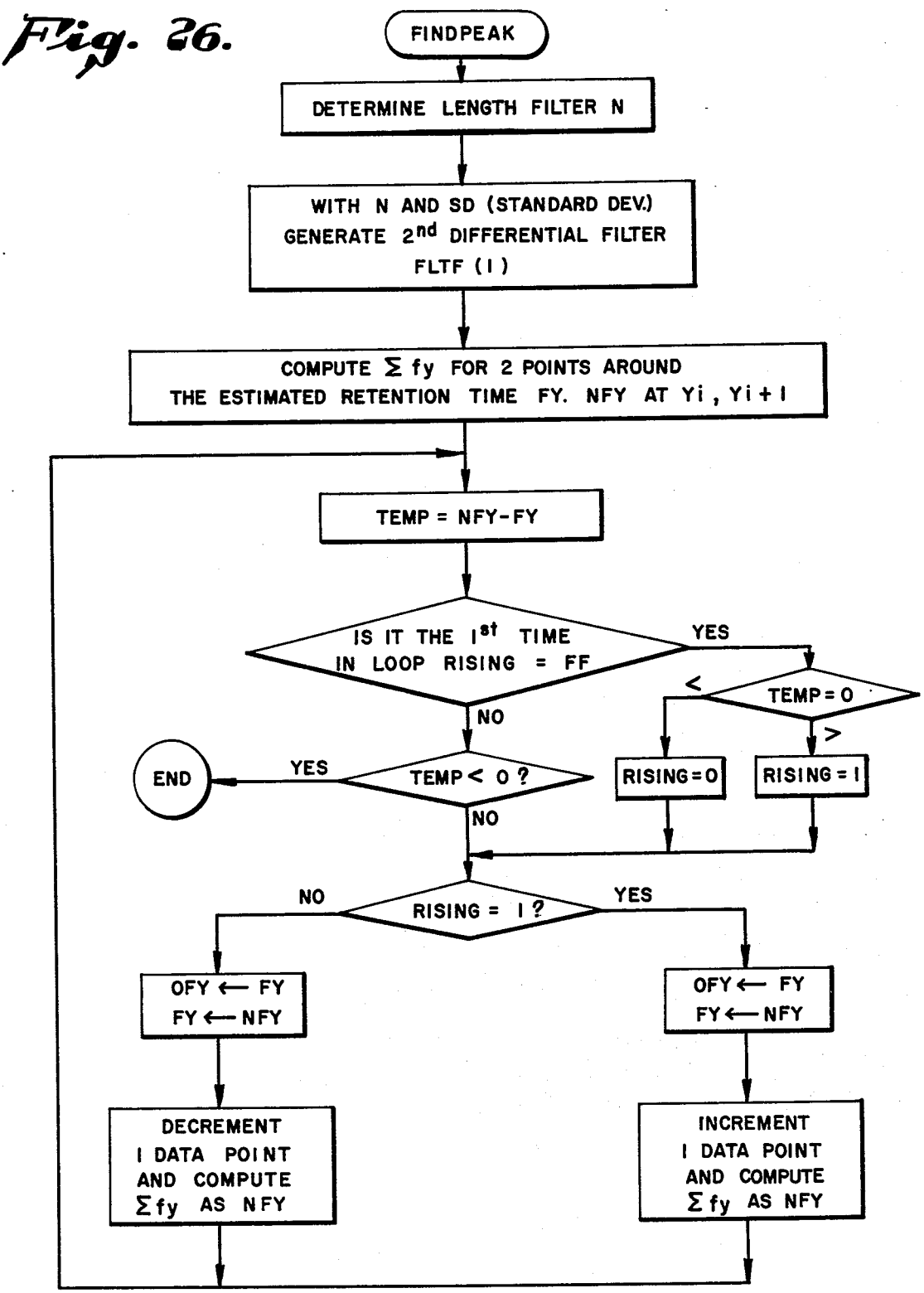
Figure 27:
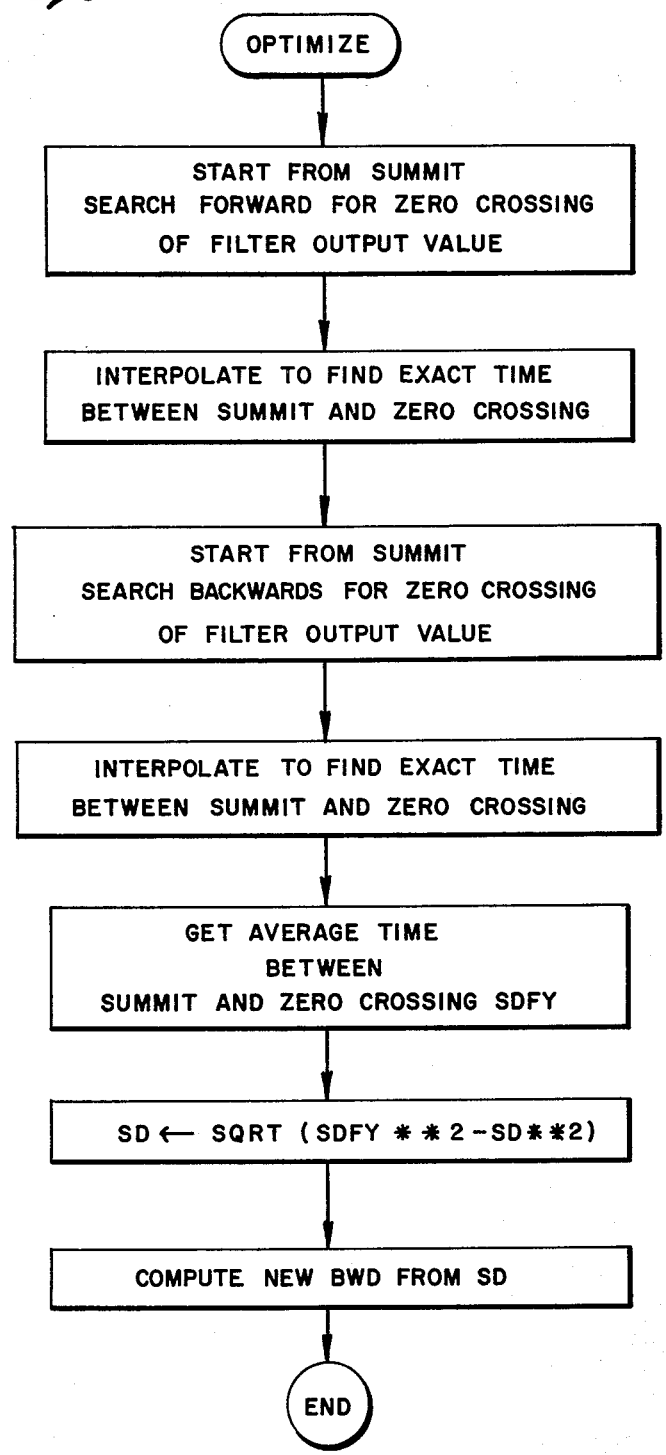
Figure 28:
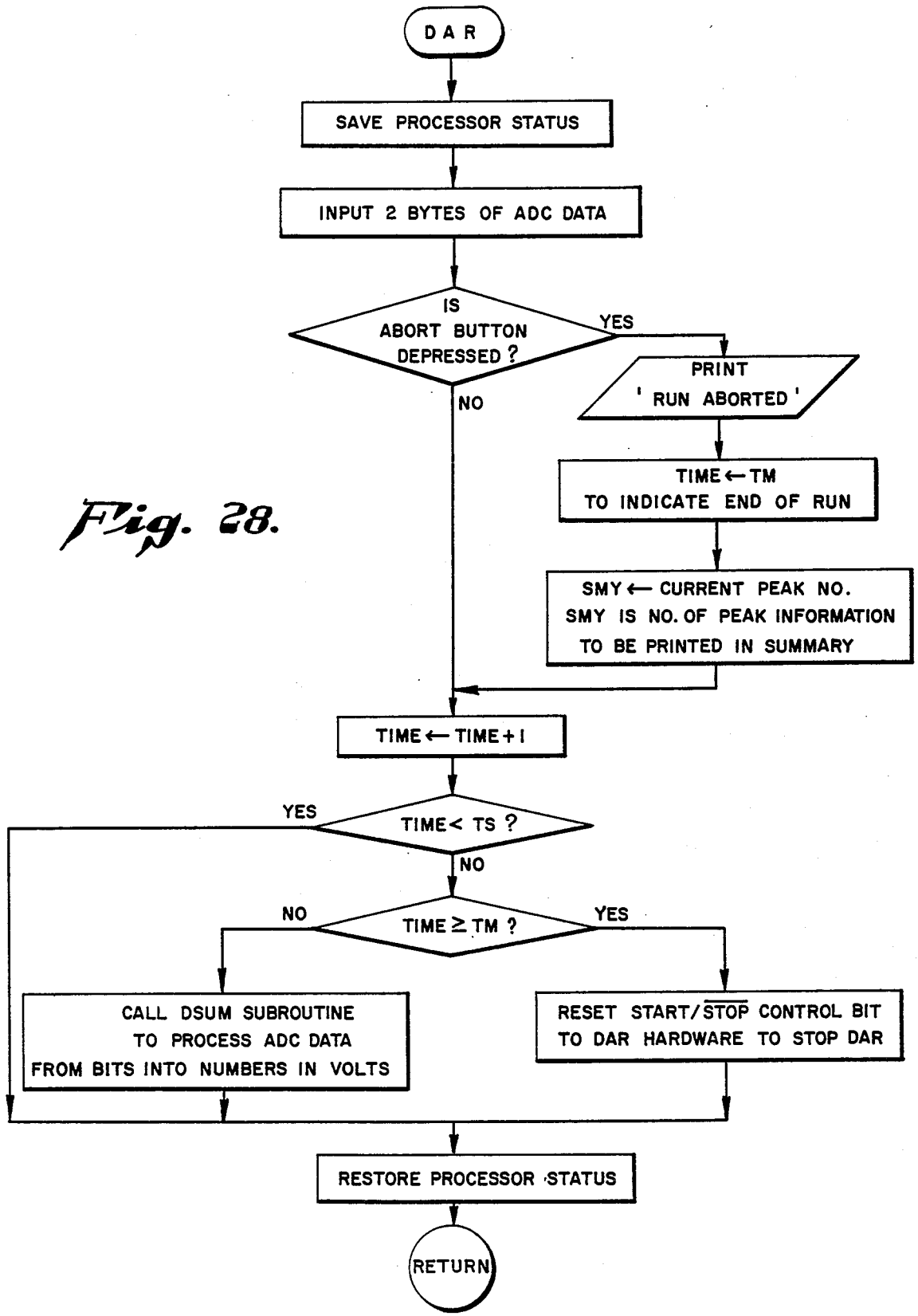
Figure 29:
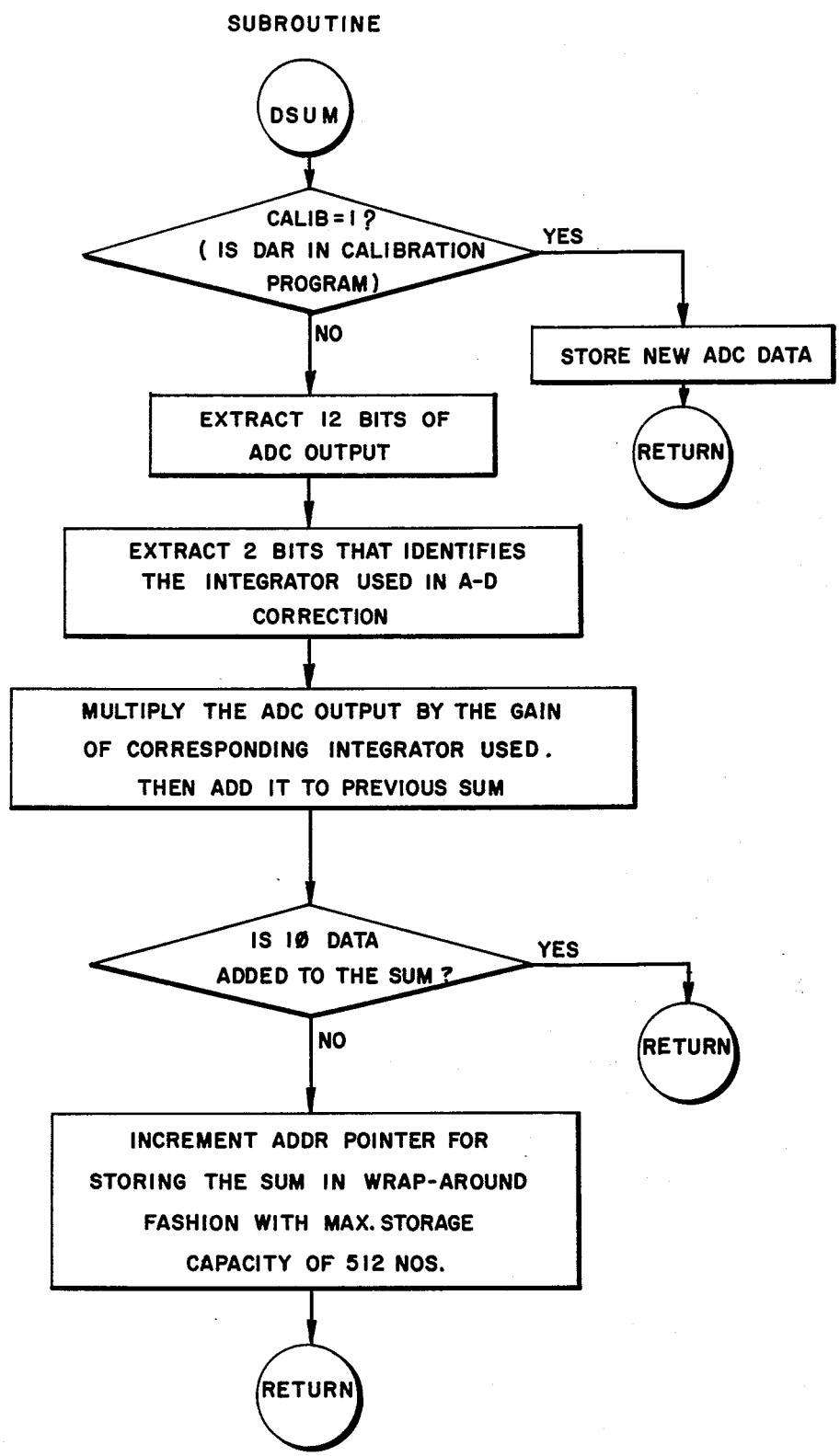

By performing a discrete convolution on data D of FIG. 4, the filter output F(X) can be obtained as shown in FIG. 6:

$$F(X) = \sum_{K=-6\sigma}^{6\sigma} f(x)D(X + x) \qquad (II)$$

After all of the peak parameters are set up and the data acquisition hardware is calibrated, the sample analysis program "EXPR" 58 is run. The first sample is a standard that contains all of the chromatographic peaks to be measured. By specifying the injection as a standard sample, the program learns the characteristic of each peak by optimizing the peak width and retention time estimates entered in the "SETUP" program 52. After the retention time clock starts, the data acquisition routine begins storing data for the first peak data window which is derived to give 19$\sigma$ around the estimated retention time so as to allow $\pm 3\frac{1}{2}\sigma$ shifts in retention time between samples. The analysis program idles until all the data are collected and stored over the 19$\sigma$ range. The peak analysis is then begun.

With the estimated $\sigma_f$, the second differential filter (I) is generated, and the filter output F(X) (II) is computed at the predicted retention time. By increasing X by one data point and comparing F(X+1) to F(X), the program searches in the direction of increasing or decreasing X to locate the maximum F(X), i.e., the "best fit".

If the injection is specified as a standard sample, a peak width estimate optimization is performed. The convolution between the second differential filter and a Gaussian chromatographic peak is FIG. 6 and can be shown to be the second differential of a Gaussian with mean X and standard deviation:

$$\sigma_F = \sqrt{\sigma_f^2 + \sigma_D^2} \qquad (III)$$

With a quadratic interpolation technique, the precise spacing between the zero crossing points of F(X) can be found, which are X$\pm\sigma_F$. A better estimate of the actual standard deviation of the data $\sigma_D$ is therefore given by the relation:

$$\sigma_D^2 = \sigma_F^2 - \sigma_f^2 \qquad (IV)$$

By repeating the convolution with $\sigma_f$ equal to this estimate of $\sigma_D$, a closer estimate of $\sigma_D$ can be found. This iterative process converges rapidly (generally to within 0.1% in four iterations). The final estimate of $\sigma_f$ is then used for subsequent sample analysis by "EXPR" 58, and is also converted back to half-height peak width to be printed out on the terminal.

After each peak is located, the exact size and retention time are estimated by quadratic interpolation between values of F(X). Similarity of the peak shape to that of a Gaussian curve of the same width is indicated by the correlation coefficient, r. This allows an assessment to be made of the statistical significance of the peak, using the variance ratio F, where:

$$F_{n-2,1} = \frac{(n-2)r^2}{1-r^2} \qquad (V)$$

and n is the number of data points in the correlation. If the F statistic for the peak is less than (P$\geq$0.05), the message "peak not found" is printed. Upon completion of the sample run, a summary of each peak is printed on the terminal. The summary contains the estimated peak width and size, the abundance relative to the internal standard peak, the correlation coefficient, and the interpolated retention time of the peak summit.

Wherefore, having thus described our invention, we claim:

1. In the quantitative analysis of a series of samples as to the contents therof in apparatus producing an output signal reflecting the quantity of a component as a peak of substantially Gaussian shape at a fixed time associated with the component, the improved method comprising the steps of:
   (a) injecting into the apparatus a standard sample containing a known amount of the compound to be analyzed;
   (b) measuring the time to the output of a signal peak associated with the compound to be analyzed to establish the retention time of the apparatus associated therewith;
   (c) saving said established retention time;
   (d) establishing a data filter by scaling a Gaussian based curve to the curve of said signal peak;
   (e) injecting into the apparatus a series of samples containing unknown amounts of said compound to be analyzed;
   (f) for each sample of said series, sequentially convolving said data filter to the output signal for a sequence of time divisions on either side of and in close proximity to said saved retention time following the injection of said sample to establish a figure of merit reflecting the size of the output signal waveform at its peak to said data filter curve; and,
   (g) determining the quantity of component for each of said samples of said series as a function of said figure of merit relative to the known quantity in said standard sample.

2. The method of claim 1 and additionally: establishing a correlation coefficient reflecting the accuracy of the best fit curve from said data filter used to establish said figure of merit whereby the probability of said figure of merit being an accurate reflection of the quantity of the component in the sample can be determined.

3. The method of claim 1 or claim 2 wherein: said data filter is a finite impulse response filter and has the shape of a second differential Gaussian.

4. The method of claim 3 wherein: said data filter has a length of $12\sigma$.

5. The method of claim 3 wherein: said filter function is expressed as $$f(x) = \left(\frac{2}{\sigma}\right)^{3/2}\left(1 - \frac{x^2}{\sigma^2}\right) e^{-\frac{x^2}{2\sigma^2}}$$

6. The method of claim 5 wherein: the data is convolved for a window about said retention time derived to give $19\sigma$ around said retention time.

7. The method of claim 2 wherein: said filter function is expressed as $$f(x) = \left(\frac{2}{\sigma}\right)^{3/2}\left(1 - \frac{x^2}{\sigma^2}\right) e^{-\frac{x^2}{2\sigma^2}};$$

and, said correlation coefficient r is used to generate the variance ratio F of the two peaks expressed as $$F_{n-2,1} = \frac{(n-2)r^2}{1-r^2}$$

where n is the number of data points in the correlation.

8. The method of claim 1 wherein further data acquisition hardware is provided, from which samples are injected into the apparatus; and the actual filtering is done by using a finite impulse response filter with a length of $12\sigma$ and the shape of a second differential Gaussian f(x) expressed as $$f(x) = \left(\frac{2}{\sigma}\right)^{3/2}\left(1 - \frac{x^2}{\sigma^2}\right) e^{-\frac{x^2}{2\sigma^2}} \quad (I)$$

by performing a discrete convolution on the data to obtain the filter output F(X) expressed as $$F(X) = \sum_{K=-6\sigma}^{6\sigma} f(x)D(X + x) \quad (II)$$

according to the steps:
   (a) setting up all of the peak parameters and calibrating the data acquisition hardware;
   (b) performing an analysis on the known sample in order to learn characteristics of the compound of interest by specifying the injection as a standard sample;
   (c) establishing the characteristic of each peak of the standard sample by optimizing the peak width and retention time estimates;
   (d) after the retention time clock starts, storing data for the first peak data window which is derived to give $19\sigma$ around an estimated retention time so as to allow $\pm 3\frac{1}{2}\sigma$ shifts in retention time between samples;
   (e) collecting and storing all the data over the $19\sigma$ range;
   (f) beginning a peak analysis on the data of the standard sample by using the estimated $\sigma_f$ to generate the second differential filter (I);
   (g) then computing the filter output F(X) (II) at the predicted retention time;
   (h) sequentially increasing X by one data point and comparing F(X+1) to F(X) to search in the direction of increasing or decreasing X to locate the maximum F(X) or "best fit";
   (i) performing a peak width estimate optimization first utilizing the fact that the convolution between the second differential filter and a Gaussian chromatographic peak is the second differential of a Gaussian with mean X and standard deviation $$\sigma_F = \sqrt{\sigma_f^2 + \sigma_D^2} \quad (III)$$

(j) employing a quadratic interpolation technique, finding the precise spacing between the zero crossing points of F(X), which are $X \pm \sigma_F$;
   (k) making a better estimate of the actual standard deviation of the data $\sigma_D$ by the relation $$\sigma_D^2 = \sigma_F^2 - \sigma_f^2 \quad (IV)$$

(l) repeating the convolution with $\sigma_f$ equal to this estimate of $\sigma_D$ to find a closer estimate of $\sigma_D$;

(m) repeating this iterative process until it converges;

(n) saving the final estimate of $\sigma_f$ for the best fit of the sample peak curve for unknown data comparison;

(o) for each unknown sample, computing the regression coefficient between the data and the previously scaled filter in sequential steps throughout the window until a peak is found as indicated by the regression coefficient being maximized; and, (p) after each peak is located, estimating the exact size and retention time by quadratic interpolation between values of F(X).

9. The method of claim 8 and additionally comprising the steps of:

(a) indicating the similarity of the peak shape to that of a Guassian curve of the same width by the correlation coefficient, r;

(b) assessing the statistical significance of the peak, using the variance ratio F, where:

$$F_{n-2,1} = \frac{(n-2)r^2}{1-r^2} \quad (V)$$

and n is the number of data points in the correlation; and, (c) if the F statistic for the peak is less than ($P \geq 0.05$), indicating "peak not found".

10. In apparatus for the quantitative analysis of samples as to the contents thereof wherein the apparatus has an input for the injection of a sample and an output producing a signal reflecting the quantity of a component as a peak of substantially Gaussian shape at a fixed time associated with the component following injection, the improvement for allowing rapid and accurate analysis of series of samples for the same component comprising:

(a) means operatively connected to the apparatus for an operator to designate whether a sample being analyzed is a standard sample or an unknown sample;

(b) means operatively connected to said designation means and the output for storing characteristic data about a sample when an operator designates the sample as a standard sample; and, (c) means operatively connected to said designation means, said storing means and the output for calculating a figure of merit related to the quantity of unknown component in a sample as a function of the relationship of the stored standard sample characteristics to the characteristics of the sample's output signal characteristics when an operator designates the sample as an unknown sample whereby the derived value of the unknown component is a function of learned characteristics about such components.

11. The improvement of claim 10 wherein:
said characteristic data storage means stores the retention time between injection of the sample and the peak in the output signal associated with the component of interest.

12. The improvement of claim 11 and additionally comprising:

means operably connected to said characteristic data storage means for an operator to designate a time window only during which a peak is searched for.

13. The improvement of claim 10 or claim 11 wherein:
said characteristic data storage means stores data associated with the shape of the curve of the peak for the component of interest.

14. The improvement of claim 13 wherein:
said characteristic data storage means stores parameters defining a Gaussian based curve.

15. The improvement of claim 14 wherein:
said Gaussian based curve is a second differential Gaussian.

16. The improvement of claim 15 wherein:
said calculating means employs a finite impulse response data filter defined by said stored parameters and convolves said filter against unknown sample data to get a best fit to the shape of the peak of the signal for the unknown sample.

17. The improvement of claim 16 wherein:
said data filter has a length of $12\sigma$.

18. The improvement of claim 16 wherein:
said filter function is expressed as $$f(x) = \left(\frac{2}{\sigma}\right)^{3/2} \left(1 - \frac{x^2}{\sigma^2}\right) e^{-\frac{x^2}{2\sigma^2}}$$

19. The improvement of claim 18 wherein:
the data is convolved for a window about said retention time derived to give $19\sigma$ around said retention time.

20. The improvement of claim 18 and additionally comprising:

means operatively connected to said calculating means for establishing a correlation coefficient reflecting the accuracy of the best fit curve from said data filter used to establish said figure of merit whereby the probability of said figure of merit being an accurate reflection of the quantity of the component in the sample can be determined.

21. The improvement of claim 20 wherein:
said correlation coefficient r is used to generate the variance ratio F of the two peaks expressed as $$F_{n-2,1} = \frac{(n-2)r^2}{1-r^2}$$

where n is the number of data points in the correlation.

22. The improvement of claim 10 and additionally comprising:

data acquisition hardware for supplying samples to the input of said apparatus;

logic means connected to said designation means, said characteristic storing means and said calculating means for accomplishing the actual filtering by using a finite impulse response filter with a length of $12\sigma$ and the shape of a second differential Gaussian f(x) expressed as $$f(x) = \left(\frac{2}{\sigma}\right)^{3/2} \left(1 - \frac{x^2}{\sigma^2}\right) e^{-\frac{x^2}{2\sigma^2}} \quad (I)$$

by performing a discrete convolution on the data to obtain the filter output F(X) expressed as $$F(X) = \sum_{K=-6\sigma}^{6\sigma} f(x) D(X + x) \quad (II)$$

according to the steps:
(a) setting up all of the peak parameters and calibrating the data acquisition hardware;
(b) performing an analysis on the known sample in order to learn the characteristics of the compound of interest by specifying the injection as a standard sample;
(c) establishing the characteristic of each peak of the standard sample by optimizing the peak width and retention time estimates;
(d) after the retention time clock starts, storing data for the first peak data window which is derived to give $19\sigma$ around an estimated retention time so as to allow $\pm 3\frac{1}{2}\sigma$ shifts in retention time between samples;
(e) collecting and storing all the data over the $19\sigma$ range;
(f) beginning a peak analysis on the data of the standard sample by using the estimated $\sigma_f$ to generate the second differential filter (I);
(g) then computing the filter output F(X) (II) at the predicted retention time;
(h) sequentinally increasing X by one data point and comparing F(X+1) to F(X) to search in the direction of increasing or decreasing X to locate the maximum F(X) or "best fit";
(i) performing a peak width estimate optimization first utilizing the fact that the convolution between the second differential filter and a Gaussian chromatographic peak is the second differential of a Gaussian with mean X and standard deviation $$\sigma_F = \sqrt{\sigma_f^2 + \sigma_D^2} \quad (III)$$

(j) employing a quadratic interpolation technique, finding the precise spacing between the zero crossing points of F(X), which are $X \pm \sigma_F$;
(k) making a better estimate of the actual standard deviation of the data $\sigma_D$ by the relation $$\sigma_D^2 = \sigma_F^2 - \sigma_f^2 \quad (IV)$$

(l) repeating the convolution with $\sigma_f$ equal to this estimate of $\sigma_D$ to find a closer estimate of $\sigma_D$;
(m) repeating this iterative process until it converges;
(n) saving the final estimate of $\sigma_f$ for the best fit of the sample peak curve for unknown data comparison;
(o) for each unknown sample, computing the regression coefficient between the data and the previously scaled filter in sequential steps throughout the window until a peak is found as indicated by the regression coefficient being maximized; and,
(p) after each peak is located, estimating the exact size and retention time by quadratic interpolation between values of F(X).

23. The improvement of claim 22 wherein said logic means additionally accomplishes the steps of:
(a) indicating the similarity of the peak shape to that of a Gaussian curve of the same width by the correlation coefficient, r;
(b) assessing the statistical significance of the peak, using the variance ratio F, where:

$$F_{n-2,1} = \frac{(n-2)r^2}{1-r^2} \quad (V)$$

and n is the number of data points in the correlation; and,
(c) if the F statistic for the peak is less than ($P \geq 0.05$), indicating "peak not found".

* * * * *